US007951406B2

(12) United States Patent
Van Haaften

(10) Patent No.: US 7,951,406 B2
(45) Date of Patent: May 31, 2011

(54) **THERAPEUTIC COMPOUNDS ISOLATED FROM *CALOMERIA AMARANTHOIDES***

(75) Inventor: Caroline Van Haaften, Forest Lodge (AU)

(73) Assignee: Caroline Van Haaften (NL)

( * ) Notice: Subject to any disclaimer, the term of this patent is extended or adjusted under 35 U.S.C. 154(b) by 182 days.

(21) Appl. No.: 11/722,642

(22) PCT Filed: Dec. 23, 2005

(86) PCT No.: PCT/IB2005/003874
§ 371 (c)(1),
(2), (4) Date: Mar. 11, 2008

(87) PCT Pub. No.: WO2006/067603
PCT Pub. Date: Jun. 29, 2006

(65) Prior Publication Data
US 2008/0233214 A1    Sep. 25, 2008

(30) Foreign Application Priority Data

Dec. 23, 2004  (AU) ............................... 2004907275
Jan. 28, 2005  (AU) ............................... 2005900353

(51) Int. Cl.
*A61K 36/00*  (2006.01)
(52) U.S. Cl. ...................................................... 424/725
(58) Field of Classification Search .................. None
See application file for complete search history.

(56) References Cited

FOREIGN PATENT DOCUMENTS

| KR | 20040107185 A | 12/2004 |
| WO | 94/08904 | 4/1994 |
| WO | 00/27388 | 5/2000 |

OTHER PUBLICATIONS

Kamb (Nature Reviews: Drug Discovery (2005), vol. 4, pp. 161-165).*
Zdero (Phytochemistry (1991), vol. 30, No. 8, pp. 2643-2650).*
Dirsch V, et al., "Cytotoxic sesquiterpene lactones mediate their death-inducing effect in leukemia T cells by triggering apoptosis," Planta Med. 67:557-559 (2001).
Konishi T, et al., "Antiproliferative sesquiterpene lactones from the roots of *Inula helenium*," Biol. Pharm. Bull. 25:1370-1372 (2002).
Spiridonvo N, et al., "Cytotoxicity of some Russian ethnomedicinal plants and plant compounds," Phytother. Res. 19:428-432 (2005).
"Lymphocytic Leukemia P388—Protocol 1.200," Cancer Chemo. Reports 3:9, 33-35, 47-52 (1972).
Ando M, et al., "Studies on the synthesis of sesquiterpene lactones. 10. Improved synthesis of (+)-tuberiferin and the related α-methylene γ-lactones and their biological activities," J. Org. Chem. 52:4792-4796 (1987).
Ando M, et al., "Synthesis of functionalized endocyclic α,β-unsaturated and α-methylene eudesmanolides," J. Org. Chem. 56:6235-6238 (1991).
Bohlmann F, et al., "New sesquiterpene lactones from *Inula* species," Phytochemistry 17:1165-1172 (1976).
Bohlmann F, et al., "New sesquiterpene lactones, geranyllinalol derivatives and other constituents from *Geigeria* species," Phytochemistry 21:1679-1691 (1982).
Cantrell C, et al., "Antimycobacterial eudesmanolides from *Inula helenium* and *Rudbeckia subtomentosa*," Planta Med. 65:351-355 (1999).
Carda M, et al., "Total synthesis of rothin-A and rothin-B," Tetrahedron 42:3655-3662 (1986).
Dupuis G & Brisson J, "Toxic effect of alantolactone and dihydroalantolactone in in vitro cultures of leukocytes," Chem. Biol. Interact. 15:205-217 (1976).
Ellmauerer E, et al., "6β-lactonized xanthanolides from *Ratibida* species," Phytochemistry 26:159-163 (1987).
Jakupovic J, et al., "Rudbeckiolid, ein dimeres Sesquiterpenlacton aus *Rudbeckia laciniata*," Liebigs Annalen der Chemie 1986:1474-1477 (1986).
Jakupovic J, et al., "Sesquiterpene lactones and other constituents from *Cassinia*, *Actinobole* and *Anaxeton* species," Phytochemistry 27:3831-3839 (1988).
Lang G, et al., "Antiplasmodial activities of sesquiterpene lactones from *Eupatorium semialatum*," Z. Naturforsch. 57:282-286 (2002).
Li W-D & Gao Z-H, "A novel stereocontrolled approach to eudesmanolides: total synthesis of (+/−)-gallicadiol and (+/−)-isogallicadiol," Org. Lett. 7:2917-2920 (2005).
Maćias F, et al., "Studies on the stereostructure of eudesmanolides from *Umbelliferae*: synthesis of 11β-angeloyloxy-α-santonin," Tetrahedron 18:5439-5450 (1994).
Maćias F, et al., "Studies on the stereostructure of eudesmanolides from *Umbelliferae*: total synthesis of (+)-decipienin A," Tetrahedcron 56:3409-3414 (2000).
Sanz Durina M, et al., "Sesquiterpenes from *Tessaria absinthioides*," Phytochemistry 44:897-900 (1997).
Tada M, et al., "Total synthesis of three eudesman-12,8-olides, (±)-isoalantolactone, (±)-dihydrocallitrisin and (±)-septuplinolide; structure revision of septuplinolide," J. Chem. Soc. Perkin Trans. 1:239-247 (1993).
Tanaka N, et al., "Chemical investigations of the ingredients of *Xanthium canadense* MILL," Chem. Pharm. Bull. 24:1419-1421 (1976).
Wu C, et al., "Antiproliferative activities of parthenolide and golden feverfew extract against three human cancer cell lines," J. Med. Food 9:55-61 (2006).
Zdero C, et al., "The first 12.8 β-germacrolide and other constituents from Bolivian *Stevia* species," Phytochemistry 27:2835-2842 (1988). Zdero C, et al., "Eremophilane derivatives and other constituents from *Haeckeria* species and further Australian Inuleae," Phytochemistry 30:2643-2650 (1991).
Zoretic P, et al., ",Sesquiterpene synthesis. Studies relating to the synthesis of ()-dugesialactone," J. Org. Chem. 47:1327-1329 (1982).
Bohlmann F & Zdero C, "Ein neues sesquiterpenlacton aus Dugesia mexicana Gray," Chemische Berichte 109:2651-2652 (1976).

* cited by examiner

*Primary Examiner* — Susan C Hoffman
(74) *Attorney, Agent, or Firm* — Quarles & Brady LLP

(57) ABSTRACT

The present invention relates to extracts and compounds which are isolated from *Calomeria amaranthoides*, and to derivatives and analogues of such compounds, which demonstrate cytotoxic activity against a variety of cell types exhibiting hyperproliferative cell division.

6 Claims, 22 Drawing Sheets

| No. | RT | Area | Conc 1 | BC |
| --- | --- | --- | --- | --- |
| 1 | 1.33 | 953518 | 73.894 | BV |
| 2 | 1.78 | 1417 | 0.110 | TBB |
| 3 | 2.04 | 2093 | 0.162 | TBB |
| 4 | 3.09 | 70140 | 5.436 | BB |
| 5 | 3.57 | 2112 | 0.164 | TBB |
| 6 | 4.06 | 11373 | 0.881 | BB |
| 7 | 9.63 | 6226 | 0.483 | BB |
| 8 | 11.47 | 17537 | 1.359 | BB |
| 9 | 12.60 | 3016 | 0.234 | BB |
| 10 | 13.17 | 3004 | 0.233 | BB |
| 11 | 19.13 | 10563 | 0.819 | BB |
| 12 | 26.79 | 209375 | 16.226 | BB |
|  |  | 1290374 | 100.000 |  |

Peak rejection level: 0

Page Indicator 1 / 3

| No. | RT | Area | Conc 1 | BC |
|---|---|---|---|---|
| 1 | 1.32 | 946784 | 78.151 | MC |
| 2 | 1.79 | 8016 | 0.662 | MC |
| 3 | 3.09 | 46910 | 3.872 | MC |
| 4 | 3.36 | 26258 | 2.167 | MC |
| 5 | 3.58 | 3061 | 0.253 | MC |
| 6 | 3.83 | 6128 | 0.506 | MC |
| 7 | 5.59 | 19205 | 1.585 | MC |
| 8 | 7.99 | 9429 | 0.778 | MC |
| 9 | 9.65 | 1956 | 0.162 | MC |
| 10 | 12.63 | 5278 | 0.436 | MC |
| 11 | 13.15 | 4088 | 0.337 | MC |
| 12 | 15.26 | 24562 | 2.028 | MC |
| 13 | 19.20 | 15561 | 1.284 | MC |
| 14 | 21.58 | 5846 | 0.483 | MC |
| 15 | 26.69 | 5886 | 0.486 | MC |
| 16 | 27.99 | 5414 | 0.447 | MC |
| 17 | 32.60 | 13419 | 1.108 | MC |
| 18 | 39.27 | 26056 | 2.151 | MC |
| 19 | 45.80 | 6073 | 0.501 | MC |
| 20 | 53.28 | 31544 | 2.604 | MC |
|   |   | 1211474 | 100.000 |   |

| No. | RT | Area | Conc 1 | BC |
|---|---|---|---|---|
| 1 | 1.31 | 938519 | 76.158 | BV |
| 2 | 1.80 | 5935 | 0.482 | MC |
| 3 | 2.90 | 0 | 0.000 | |
| 4 | 3.09 | 62404 | 5.064 | MC |
| 5 | 3.61 | 4296 | 0.349 | MC |
| 6 | 4.49 | 7970 | 0.647 | MC |
| 7 | 6.91 | 18767 | 1.523 | MC |
| 8 | 9.56 | 3875 | 0.315 | MC |
| 9 | 12.55 | 5956 | 0.483 | MC |
| 10 | 13.17 | 3124 | 0.254 | MC |
| 11 | 14.43 | 10865 | 0.882 | MC |
| 12 | 19.08 | 15540 | 1.261 | MC |
| 13 | 21.54 | 24696 | 2.004 | MC |
| 14 | 27.91 | 14523 | 1.179 | MC |
| 15 | 32.53 | 26242 | 2.129 | MC |
| 16 | 39.19 | 20511 | 1.664 | MC |
| 17 | 45.72 | 38032 | 3.086 | MC |
| 18 | 52.91 | 31063 | 2.521 | MC |
| | | 1232318 | 100.000 | |

Ovarian Ca. Cell line
| | | | |
|---|---|---|---|
| 24 | 98 | 85 | 77 |
| 48 | 97 | 84 | 84 |
| 72 | 70 | 21 | 8 |

Human skin fibroblasts
| | | | |
|---|---|---|---|
| 24 | 89 | 73 | 78 |
| 48 | 94 | 80 | 73 |
| 72 | 97 | 88 | 61 |

Human lymphocytes
| | | | |
|---|---|---|---|
| 24 | 103 | 100 | 62 |
| 48 | 105 | 91 | 62 |
| 72 | 119 | 91 | 48 |

THERAPEUTIC COMPOUNDS ISOLATED FROM CALOMERIA AMARANTHOIDES

FIELD OF THE INVENTION

The present invention relates broadly to extracts and compounds which are isolated from *Calomeria amaranthoides* plants, and to derivatives and analogues of such compounds, which demonstrate cytotoxic activity against a variety of cell types exhibiting hyperproliferative cell division.

BACKGROUND OF THE INVENTION

*Calomeria amaranthoides*, which is more commonly known as Incense Plant or Plum Bush, is from the daisy family Asteraceae. Its appearance is somewhat similar to that of a tobacco plant, having lime-green, wrinkly leaves from which emit an aromatic scent and are sticky to touch. The plant is biennial, and flowers in a range of colours from a whitish pink, a range of pink shades, and the most commonly occurring flower colour, red. The flower heads are plumed in appearance and are highly valued in the cut-flower industry.

*Calomeria amaranthoides* is a native Australian plant, and grows along river flats and in coastal regions of New South Wales and Victoria. The leaves of the plants are part of the diet of native Australian animals living in these areas, and it is apparent that there is little or no toxicity present in animals relying on these plants as a food source. This information, combined with the handling of the flowers of *Calomeria amaranthoides* by humans during harvesting and floral arrangement, provides an expectation of low toxicity to mammals in the use of *Calomeria amaranthoides* extracts as drugs.

The present inventor has now determined that extracts of *Calomeria amaranthoides* exhibit potent and selective cytotoxic properties towards certain cell types exhibiting hyperproliferative cellular division, and in particular, to cancerous cell types, but not to a variety of normal cells.

SUMMARY OF THE INVENTION

According to a first aspect, the present invention provides a compound of Formula I

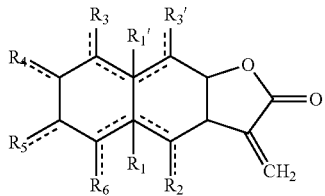

I or the pharmaceutically acceptable salts thereof, wherein
$R_1$-$R_6$ are independently selected from the group consisting of:
H, OH, halo, $CH_2$, $(C_1$-$C_8)$alkyl-, $(C_1$-$C_8)$alkyl-O—, HO—$(C_1$-$C_8)$alkyl-, NC—, $H_2N$—, $H_2N$—$(C_1$-$C_8)$alkyl-, HO—(C=O)—, HO—(C=O)—$(C_1$-$C_8)$alkyl, $(C_1$-$C_8)$-alkyl(C=O)—, $(C_1$-$C_8)$alkyl-(C=O)—$(C_1$-$C_8)$alkyl-, $H_2N$—(C=O)—, $H_2N$—(C=O)—$(C_1$-$C_8)$alkyl- and cycloalkyl-, with the proviso that when $R_1$=$CH_3$; $R_{1'}$=$CH_3$; $R_2$=H, H; $R_3$=H, H; $R_{3'}$=H, H; $R_4$=H, H; $R_5$=O; $R_6$≠$CH_3$ ($\Delta_{4,5}$);

when $R_1$=H; $R_{1'}$=—; $R_2$=$CH_3$; $R_3$=H; $R_{3'}$=H, H; $R_4$=H, H; $R_5$=H, H; $R_6$≠$CH_3$ ($\Delta_{1,10}$);

when $R_1$=$CH_3$; $R_{1'}$=H; $R_2$=H, H; $R_3$=H, H; $R_{3'}$=H, H; $R_4$=H, H; $R_5$=H, H; $R_6$≠$CH_2$;

when $R_1$=$CH_3$; $R_{1'}$=H; $R_2$=H, H; $R_3$=H, H; $R_{3'}$=H, H; $R_4$=H, H; $R_5$=H, H; $R_6$≠$CH_3$, OH;

when $R_1$=H; $R_{1'}$=$CH_3$, $R_2$=H, H; $R_3$=H, H; $R_{3'}$=H, H; $R_4$=H, H; $R_5$=H, H; $R_6$≠$CH_3$, OH;

when $R_1$=—; $R_{1'}$=$CH_3$; $R_2$=H, H; $R_3$=H, H; $R_{3'}$=H, H; $R_4$=H, H; $R_5$=O; $R_6$≠$CH_3$ ($\Delta_{4,5}$)

Examples of specific preferred compounds of Formula I are the following:

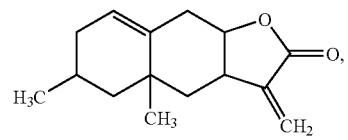

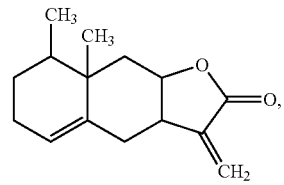

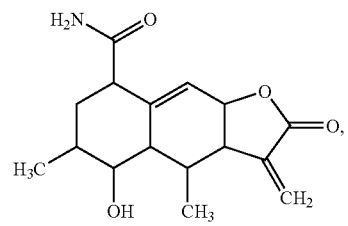

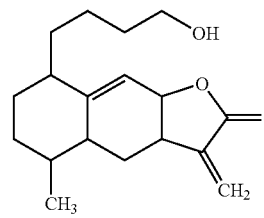

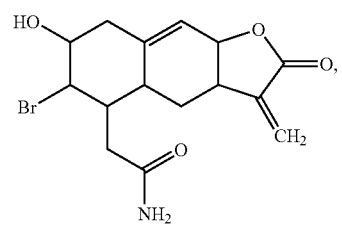

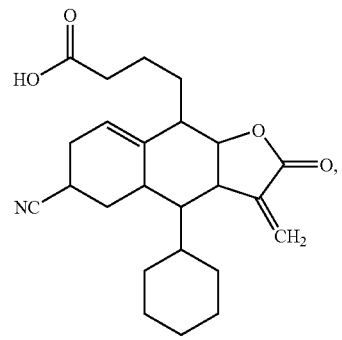

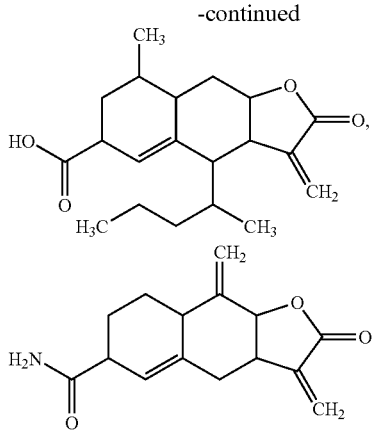

or the pharmaceutically acceptable salts thereof.

According to a second aspect of the invention, there is provided an extract of *Calomeria amaranthoides* which exhibits cytotoxic activity towards cells exhibiting conditions associated with hyperproliferative cellular division.

Preferably, the extract is derived from the leaves of *Calomeria amaranthoides*.

In one embodiment the extract is an organic solvent-derived extract. Preferably the organic solvent is selected from the group consisting of chloroform, petrol ether, dichloromethane, ethylacetate and methanol. Most preferably, the solvent is chloroform.

In a preferred embodiment, the extract exhibits a proton NMR spectrum as shown in FIG. 5A and a $C^{13}$ NMR spectrum as shown in FIG. 5B.

In another embodiment the extract is a non-polar extract.

In one embodiment, the cytotoxic activity of the extracts results from a synergistic interaction between two or more compounds within the extract.

According to a third aspect, the invention provides a pharmaceutical composition comprising a pharmaceutically effective amount of an extract according to the third aspect, and a pharmaceutically acceptable carrier.

According to a fourth aspect, the invention provides a method of inhibiting growth or eliminating cells exhibiting conditions associated with hyperproliferative cellular division comprising administering to the cells an effective amount of an extract according to the third aspect.

According to a fifth aspect, the invention provides a method of treatment or prophylaxis of a condition associated with hyperproliferative cellular division in a patient which comprises administering to the patient an effective amount of an extract according to the third aspect.

According to a sixth aspect, the invention provides the use of an extract of *Calomeria amaranthoides* according to the third aspect in the preparation of a medicament for treatment or prophylaxis of a condition in a patient associated with hyperproliferative cellular division.

According to a seventh aspect, the present invention provides a pharmaceutical composition comprising a pharmaceutically effective amount of a compound of the invention and a pharmaceutically acceptable carrier.

According to an eighth aspect, the present invention provides a method of inhibiting growth or eliminating cells exhibiting conditions associated with hyperproliferative cellular division comprising administering to the cells an effective amount of a compound of the invention.

According to a ninth aspect, the present invention provides a method of treatment or prophylaxis of a condition associated with hyperproliferative cellular division in a patient comprising administering to the patient an effective amount of a composition according to the seventh aspect.

According to a tenth aspect, the present invention provides the use of a compound according to the invention in the manufacture of a medicament for the treatment or prophylaxis of a condition associated with hyperproliferative cellular division.

Preferably, the condition associated with hyperproliferative cellular division is a solid cancer or a haematopoietic malignant cancer. More preferably, the condition is ovarian cancer.

The compounds of the invention include all conformational isomers (e.g., cis and trans isomers) and all optical isomers of compounds of Formula I and Formula II (e.g., enantiomers and diastereomers), as well as racemic, diastereomeric and other mixtures of such isomers.

In one embodiment the invention relates to derivatives and analogues of compounds isolated from extracts of *Calomeria amaranthoides* which exhibit cytotoxic activity towards cells exhibiting conditions associated with hyperproliferative cellular division.

In a further embodiment, the present invention relates to a method of inhibiting growth or eliminating cells exhibiting conditions associated with hyperproliferative cellular division comprising administering to the cells an effective amount of one or more compounds isolated from an extract of *Calomeria amaranthoides*, and/or derivatives or analogues of the one or more compounds.

According to another embodiment of the present invention there is provided a method of treatment or prophylaxis of a condition associated with hyperproliferative cellular division in a patient which comprises administering to the patient an effective amount of an extract of *Calomeria amaranthoides*, and/or one or more compounds isolated from such an extract, and/or derivatives or analogues of the one or more compounds.

According to yet another embodiment of the present invention there is provided use of one or more compounds isolated from an extract of *Calomeria amaranthoides*, and/or derivatives or analogues of the one or more compounds in the preparation of a medicament for treatment or prophylaxis of a condition in a patient associated with hyperproliferative cellular division.

According to a further embodiment the present invention provides a pharmaceutical preparation comprising a pharmaceutically effective amount of an extract from *Calomeria amaranthoides*, and/or compounds isolated from an extract of *Calomeria amaranthoides* and/or derivatives or analogues thereof, and a pharmaceutically acceptable carrier.

In a particularly preferred form, at least one of the extracts contains at least one compound selected from the group comprising eudesmanolide-like structures, particularly sesquiterpene lactones, polyacetylenes, alkaloids, coumarins, prenylated coumarins, flavonoids, p-hydroxyacetophenone, acetophenone, diterpenes, lignans (particularly difuranoid lignans) and DNA topoisomerase inhibitors, and/or derivatives or analogs of the aforementioned compounds.

BRIEF DESCRIPTION OF THE DRAWINGS

FIGS. 2L and 2M are repeat runs with different run times than FIG. 2K.

DETAILED DESCRIPTION OF THE PREFERRED EMBODIMENTS

Figure 1:
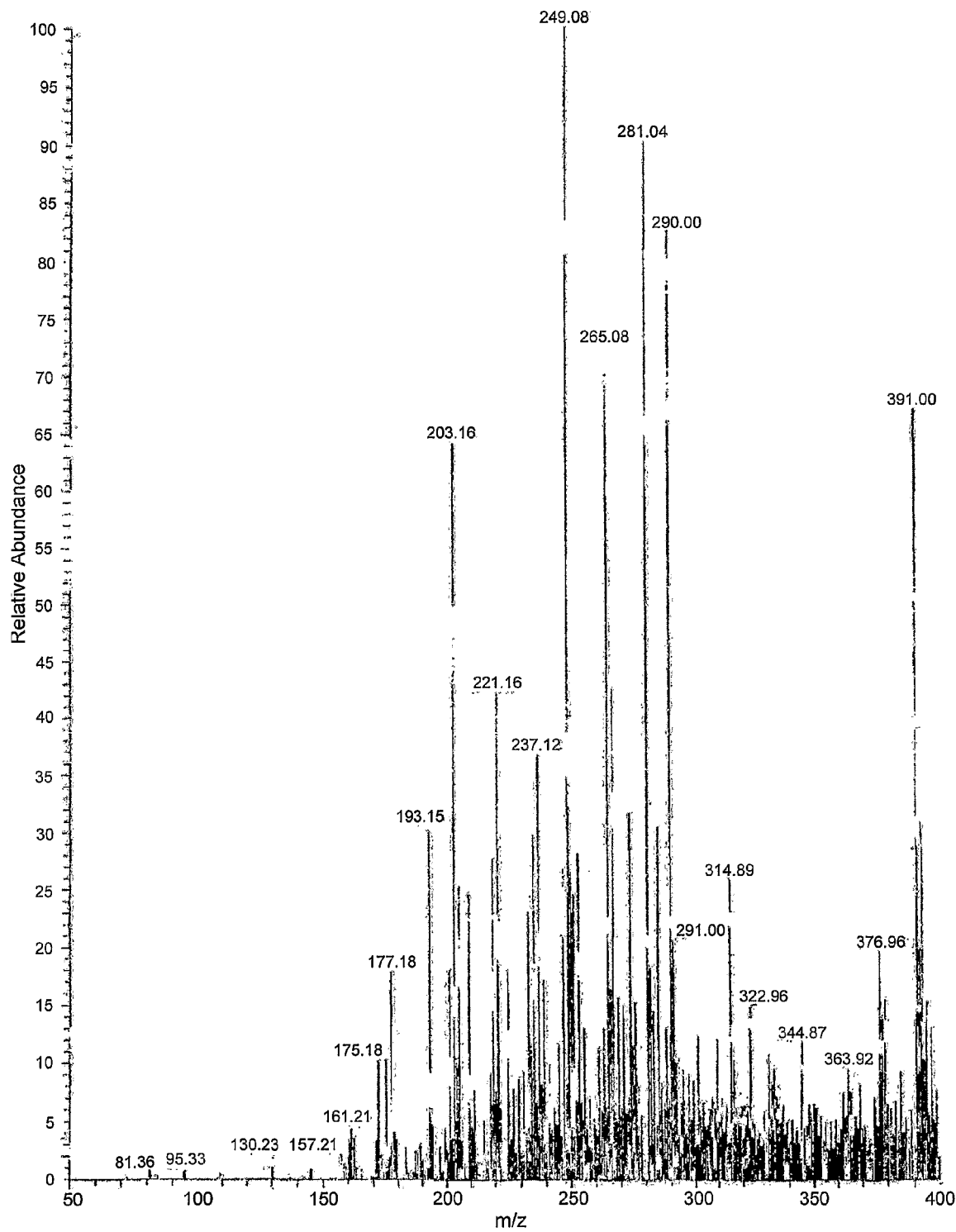
FIG. 1 shows a mass spectrometry trace of a crude chloroform extract of *Calomeria amaranthoides*.

Throughout this specification, unless the context requires otherwise, the words "comprise," "comprises" and "comprising" will be understood to imply the inclusion of a stated step or element or group of steps or elements but not the exclusion of any other step or element or group of steps or elements.

The reference to any prior art in this specification is not, and should not be taken as, an acknowledgement or any form of suggestion that the prior art forms part of the common general knowledge in Australia.

In its broadest form, the present invention relates to extracts from one or more parts of a *Calomeria amaranthoides* plant. Persons skilled in the art will appreciate that there are a number of different methods for synthesising extracts from crude plant material, starting with cutting or chopping raw plant material and exposing it to at least one solvent in order to obtain a plant extract. Alternatively, for example, the raw plant material may first be ground into a fine powder and subjected to a soxhlet extraction process.

In a further form, the invention relates to compounds isolated from extract of *Calomeria amaranthoides* plants, and derivatives or analogues thereof.

The skilled person will appreciate that there are a number of methods that may be used to isolated and characterise compounds contained in plant extracts. Samples of such methods include, but are not limited to, fractionating extracts by chromatography, with appropriate adsorbents, and purifying extracts using high-performance liquid and centrifugal countercurrent chromatography.

Furthermore, characterising pure known or new constituents can be achieved using methods such as mass spectrometry and spectroscopy, including ultraviolet, infrared, x-ray, and $^1$H and $^{13}$C nuclear magnetic resonance (NMR) spectroscopy. Once elucidated the constituents can be prepared via a synthetic process.

In another form, the extracts of *Calomeria amaranthoides* or compounds isolated from said extracts and derivatives or analogues thereof exhibit cytotoxic activity towards cells exhibiting conditions associated with hyperproliferative cellular division.

The term "condition associated with hyperproliferative cellular division" as used herein refers to any clinical condition characterised by, or otherwise involving, an increased rate of cell division relative to a normal reference rate. Conditions associated with hyperproliferative cellular division include, but are not limited to, myeloproliferative syndromes such as Langerhans cell histiocytosis, mastocytosis, mixed myeloproliferative and myelodysplastic conditions; dermal proliferative conditions such as psoriasis, non-bullous congenital ichthyosiform erythroderma. Conditions associated with hyperproliferative cellular division also include cancer, whether benign or malignant, including haematopoietic malignant cancers.

In a preferred form, the condition associated with hyperproliferative cellular division is cancer.

In a further form, the invention relates to derivatives and analogues of compounds from extracts of *Calomeria amaranthoides* which exhibit cytotoxic activity towards cells exhibiting conditions associated with hyperproliferative cellular division.

The compounds of the invention include all salts, such as acid addition salts, anionic salts and zwitterionic salts, and in particular include pharmaceutically acceptable salts as would be known to those skilled in the art. The term "pharmaceutically acceptable salt" refers to an organic or inorganic moiety that carries a charge and that can be administered in association with a pharmaceutical agent, for example, as a counter-cation or counter-anion in a salt. Pharmaceutically acceptable cations are known to those of skilled in the art, and include but are not limited to sodium, potassium, calcium, zinc and quaternary amine. Pharmaceutically acceptable anions are known to those of skill in the art, and include but are not limited to chloride, acetate, tosylate, citrate, bicarbonate and carbonate.

Pharmaceutically acceptable salts include those formed from: acetic, ascorbic, aspartic, benzoic, benzenesulphonic, citric, cinnamic, ethanesulphonic, fumaric, glutamic, glutaric, gluconic, hydrochloric, hydrobromic, lactic, maleic, malic, methanesulphonic, naphthoic, hydroxynaphthoic, naphthalenesulphonic, naphthalenedisulphonic, naphthaleneacrylic, oleic, oxalic, oxaloacetic, phosphoric, pyruvic, p-toluenesulphonic, tartaric, trifluoroacetic, triphenylacetic, tricarballylic, salicylic, sulphuric, sulphamic, sulphanilic and succinic acid.

The term "derivative" refers to a derivative of the active compound that upon administration to the recipient is capable of providing directly or indirectly, the parent compound or metabolite, or that exhibits activity itself and includes for example phosphate derivatives and sulphonate derivatives. Thus, derivatives include solvates, pharmaceutically active esters, prodrugs or the like. This also includes derivatives with physiologically cleavable leaving groups that can be cleaved in vivo to provide the compounds of the invention or their active moiety. The leaving groups may include acyl, phosphate, sulfate, sulfonate, and preferably are mono-, di- and per-acyl oxy-substituted compounds, where one or more of the pendant hydroxy groups are protected by an acyl group, preferably an acetyl group. Typically acyloxy substituted compounds of the invention are readily cleavable to the corresponding hydroxy substituted compounds.

In another embodiment, the invention relates to a method of treatment or prophylaxis of a condition in a patient associated with hyperproliferative cellular division which comprises administering to the patient an effective amount of an extract and/or one or more compounds isolated from the extract or derivative or analogue of the one or more compounds.

By "effective amount," in the context of treating or preventing a condition is meant the administration of that amount of active to an individual in need of such treatment or prophylaxis, either in a single dose or as part of a series, that is effective for treatment of, or prophylaxis against, that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The term "patient" refers to patients of human or other mammal and includes any individual it is desired to examine or treat using the methods of the invention. However, it will be understood that "patient" does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

Any suitable route of administration may be employed for providing a patient with the pharmaceutical preparations and medicaments of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed.

In another embodiment, the present invention relates to use of an extract of *Calomeria amaranthoides* and/or one or more compounds isolated from an extract of *Calomeria amaranthoides* and/or derivatives or analogues of the one or more compounds in the preparation of a medicament for treatment or prophylaxis of a condition in a patient associated with hyperproliferative cellular division.

In a further embodiment, the invention relates to pharmaceutical preparations comprising a pharmaceutically effective amount of an extract from *Calomeria amaranthoides*, and/or one or more compounds isolated from an extract of *Calomeria amaranthoides* and/or derivatives or analogues of the one or more compounds, and a pharmaceutically acceptable carrier.

By "pharmaceutically-acceptable carrier" is meant a solid or liquid filler, diluent or encapsulating substance which may be safely used for administration of the medicament or pharmaceutical preparation to a patient. Depending upon the particular route of administration, a variety of pharmaceutically-acceptable carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Pharmaceutical preparations and medicaments of the present invention suitable for oral or parenteral administration may be presented as discrete units such as capsules, sachets or tablets each containing a pre-determined amount of the extract, or one or more compounds isolated from an extract and/or derivatives or analogues thereof, as a powder or granules or as a solution or a suspension in an aqueous liquid, a non-aqueous liquid, an oil-in-water emulsion or a water-in-oil liquid emulsion. Such preparations and medicaments may be prepared by any of the methods of pharmacy but all methods include the step of bringing into association the extract as described above with the carrier which constitutes one or more necessary ingredients. In general, the pharmaceutical preparations and medicaments are prepared by uniformly and intimately admixing the extract with liquid carriers or finely divided solid carriers or both, and then, if necessary, shaping the product into the desired presentation.

A pharmaceutical composition according to the invention may be administered to a patient, prior to a symptomatic state associated with the condition, or after a symptomatic onset of the condition. The therapeutic agent/s present in the preparations and medicaments is provided for a time and in a quantity sufficient to treat that patient.

As formerly indicated, the extracts and compounds of the invention may be used in the preparation of a medicaments and pharmaceutical preparations, for use in the treatment of tumours.

In particular, the present *Calomeria amaranthoides* extracts, medicaments and pharmaceutical compositions comprising *Calomeria amaranthoides* extracts and/or compounds isolated from such extracts and/or derivatives or analogues of such compounds, are particularly effective against a variety of tumors including, for instance, solid tumors such as gastrointestinal tumors, e.g. colorectal cancer, gastro-esophageal cancer, cancer of liver and biliary tract and pancreatic cancer, prostatic cancer; testicular cancer; lung cancer; breast cancer; malignant melanoma; ovarian cancer; uterine cancer including cervical cancer; cancer of the head and neck; bladder cancer; sarcomas and osteosarcoma; Kaposi sarcoma including AIDS-related Kaposi sarcoma; renal carcinoma; hematopoietic malignant tumors such as leukemia and lymphoma, including AIDS-related lymphomas.

In addition, the extracts and compounds of the present invention or the pharmaceutical preparations or medicaments made therefrom and/or from compounds isolated from the extracts and/or derivatives or analogues thereof, may be administered according to the schedule treatment above indicated, optionally with other antitumor agents, as a combined preparation for simultaneous, separate or sequential use in anticancer therapy.

The above additional antitumor agents include, for instance, alkylating agents, topoisomerase I and II inhibitors, antimicrotubule agents and antimetabolites. As an example, specific antitumor agents are mustards such as melphalan, chlorambucil, mechlorethamine, cyclophosphamide, ifosfamide and busulfan; nitrosoureas such as carmustine, lormustine, semustine and fotemustine; tetrazines such as dacarbazine and temozolomide; aziridines such as thiotepa and mitomycin C; platinum derivatives such as cisplatin, carboplatin, oxaliplatin, nedaplatin and lobaplatin; camptothecin derivatives such as CTP-11, Topotecan, 9-amino-camptothecin, 9-nitro-camptothecin and 10,11-methylenedioxy-camptothecin; anthracycline derivatives such as doxorubicin, daunorubicin, epirubicin, nemorubicin and idarubicin; podophyllotoxin compounds etoposide and teniposide; anthraquinone derivative like mitoxantrone and losoxantrone; acridine derivatives like amsacrine and actinomaycin D; taxanes such as paclitaxel or docetaxel; vinca alkaloids such as vincristine, vinblastine, vindesine, vinorelbine; estramustine; antifolates such as metotrexate, trimetrexate, tomudex; 5-fluoropyrimides such as 5-FU, floxuridine, ftorafur and capecitabine; cytidine analogs such as cytarabine, azacitidine and gemcitabine.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

The above medicaments or pharmaceutical preparations may be administered in a manner compatible with the dosage formulation, and in such amount as is therapeutically-effective to alleviate patients from symptoms related to the condition associated with hyperproliferative cellular division, or in amounts sufficient to protect patients from developing symptoms related to the condition. The dose administered to a patient, in the context of the present invention, should be sufficient to effect a beneficial response in a patient over time such as the therapeutic or prophylactic effects mentioned above. The quantity of the therapeutic agent(s) to be administered may depend on the subject to be treated inclusive of the age, sex, weight and general health condition thereof. In this regard, precise amounts of the therapeutic agent(s) for administration will depend on the judgment of the practitioner. In determining the effective amount of the therapeutic agent to be administered in the treatment of, or prophylaxis against, the condition, the physician may evaluate progression of the condition. In any event, suitable dosages of the therapeutic agents of the invention may be readily determined by those of skill in the art. Such dosages may be in the order of micrograms to grams of the therapeutic agents of the invention.

In order that the invention may be readily understood and put into practical effect, particular preferred embodiments will now be described by way of the following non-limiting examples.

Example 1

Solvent Extraction from One- and Two-Year Old *Calomeria amaranthoides* Plants

Various solvents were used for extracting active components from one-year old plants, and two year old plants.

The leaves from the plants were dried to yield 10 grams of starting material, and the organic material they contained were extracted using a variety of solvents such as chloroform and methanol, although other suitable solvents include petroleum ether, dichloromethane, ethyl acetate, or water.

Briefly, 350 grams of leaves from *Calomeria amaranthoides* were gathered from 1-year and/or 2-year plants. The leaves were dried without sunlight at room temperature and then cut into small pieces.

The dried leaf material was soaked in chloroform and after 24-48 hours, the crude extract of the leaves was obtained. This crude extract was further adsorbed onto silica gel (60H, 5-40 μm; Merck) using column chromatography under gravity. 13 fractions were obtained from leaves of *Calomeria* plants at 1 year of age. In a repeated purification process 57 fractions were obtained from the same *Calomeria* plants, at 2 years of age.

A crude extract was also obtained using methanol for comparison to the chloroform extraction.

Example 2

Mass Spectrometry of Crude Extract of *Calomeria amaranthoides*

The crude chloroform extract obtained according to Example 2 was analysed using mass spectrometry. The results of this procedure are shown in FIG. 1.

Chemical ionisation mass spectrometry was performed with a triple stage quadropole mass spectrometer (TSQMS), ThermoFinnigan to measure the mass range. The apparatus had a positive electrospray.

Example 3

Thin-Layer Chromatography of a Crude Chloroform Extract of *Calomeria amaranthoides*

Analytical thin-layer chromatography plates used were silica gel 60F 254, on aluminium-backed sheets (0.2 mm) from Merck, Darmstadt. Silica gel 60H (5-40 um) (Merck) was used for column chromatography. Fifty-seven fractions from the crude chloroform extract of *Calomeria amaranthoides* leaves were sampled using column chromatography under gravity. An analytical sample of each fraction was spotted at the bottom of the TLC plate. The TLC plates were developed in chloroform or chloroform/methanol. The compounds were visualised under UV at 254 nm and $R_f$ calculated.

Figure 6A:
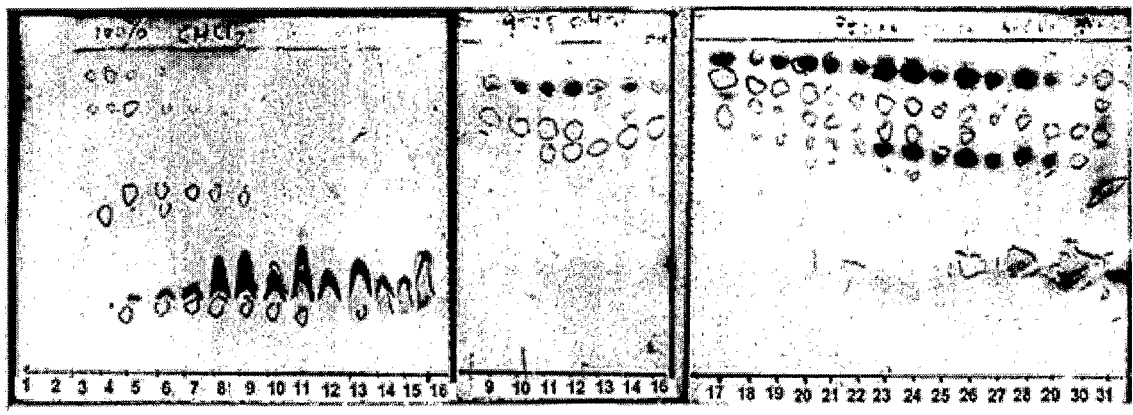
FIG. 6 shows TLC plates for 57 extracts from *Calomeria amaranthoides*.
Figure 6A:
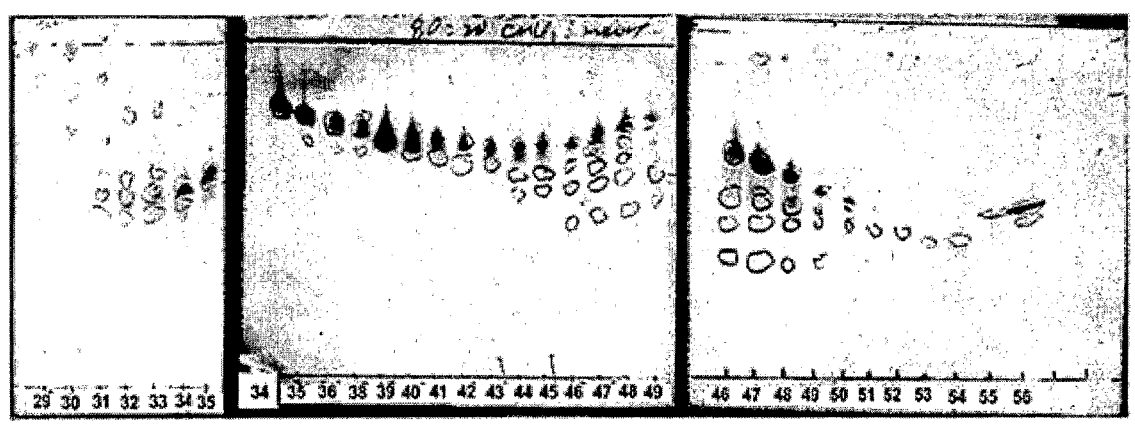
Figure 6A:
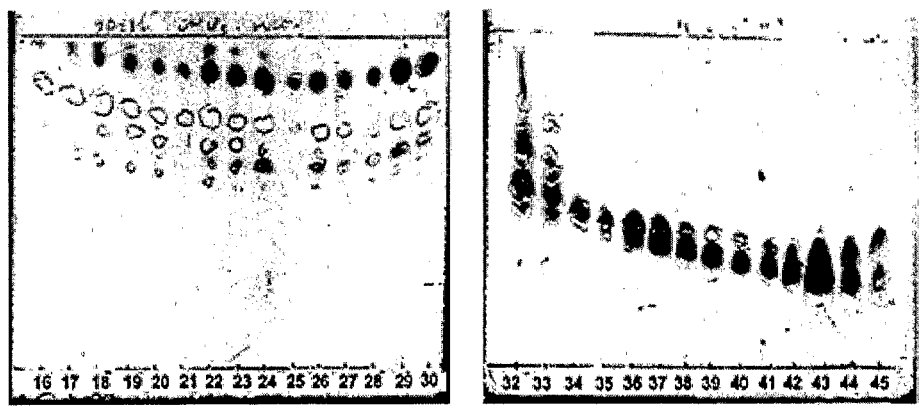

The results are shown in FIG. 6A

Example 4

Cytotoxicity of the Extracts of *Calomeria amaranthoides*

Cell Growth Inhibition Assay.

Cell Cultures of $L_{1210}$, Ovarian cancer cell lines, a Colon cell line, Normal ovarian and breast cells, human skin fibroblasts and human lymphocytes.

A mouse leukemia cell line ($L_{1210}$), five Ovarian cancer cell lines: JV, JC, JG (van Haaften-Day et al., Cancer Research 43:3725-3731, 1983) JoN and NF (van Haaften-Day et al., Cancer 65: 1753-1761, 1990), a Colon cancer cell line T/O, normal epithelial cells from ovary and breast tissue (van Haaften-Day et al., Int J Gynecol Cancer 2: 41-48, 1992), human skin fibroblasts and human lymphocytes were tested for growth inhibition and cytotoxicity with extracts of *Calomeria amaranthoides*.

$10^4$ or $5.10^4$ cells/ml were seeded in 24-well plates (Costar, USA), to a total volume of 2 ml medium/well. The medium used was RPMI 1640, supplemented with 6 mM L-glutamine, garamycin (2 ml) and 10-15% fetal calf serum (FCS) (Flow laboratories). Two wells were used as control wells. Cells were grown at 37° C. in 5% $CO_2$, and after 24 hrs were found to be still in exponential growth.

The cells were then treated with the different (dried) fractions of the plant extract or with crude extract. The samples were dissolved in DMSO and 4 μl was added to each well containing cells and 2 ml medium. The final concentration of DMSO was less than 0.02%/well Each sample was tested (in triplicate) at a final concentration of 1, 10 and 100 μg/ml.

Cells were then counted after 24, 48 and 72 hours of treatment.

Cytotoxicity of the compounds was expressed as IC50 values, following the Methylene Blue assay by Finlay et al., 1984 that is:

$$\text{cell growth percentage \%} = \frac{\text{absorbance of treated cells}}{\text{absorbance of control cells}} \times 100\%$$

Medium was removed from the wells and 200 μl methylene blue/well was added for a one-hour incubation period. Wells were then washed 3 times with water and dried for one day at room temperature. 200 µl Sarkosyl (1% in PBS, Sigma) was added and the 24 well plates were left in the incubator for 5 hours. 100 µl/well was then transferred with different tips to 96 well flat-bottom plates.

UV absorbances were read with a microplate reader at a wavelength of 595 nm.

Normal epithelial cells of ovary- and breast tissue, grown in 24 well plates and treated as above, were trypsinized after 24, 48 hours. Cell viability was counted manually, using a Neubauer haemocytometer under light microscopy. The Trypan blue exclusion method was used. A minimum of 200 cells were counted. Little effect could be seen on growth inhibition or cell viability after 48 hours with the crude extracts.

Cytotoxicity of fractionated crude extract derived from 1 year old *Calomeria* plants (13 fractions) was assessed and expressed as IC50 values using the Methylene Blue assay. The ovarian cancer cell line JV (van Haaften-Day et al. Cancer Res. 43(8), 3725-31) was used and fraction 2, 4, 6 and 8 exhibited the highest levels of cytotoxicity.

Figure 3A:
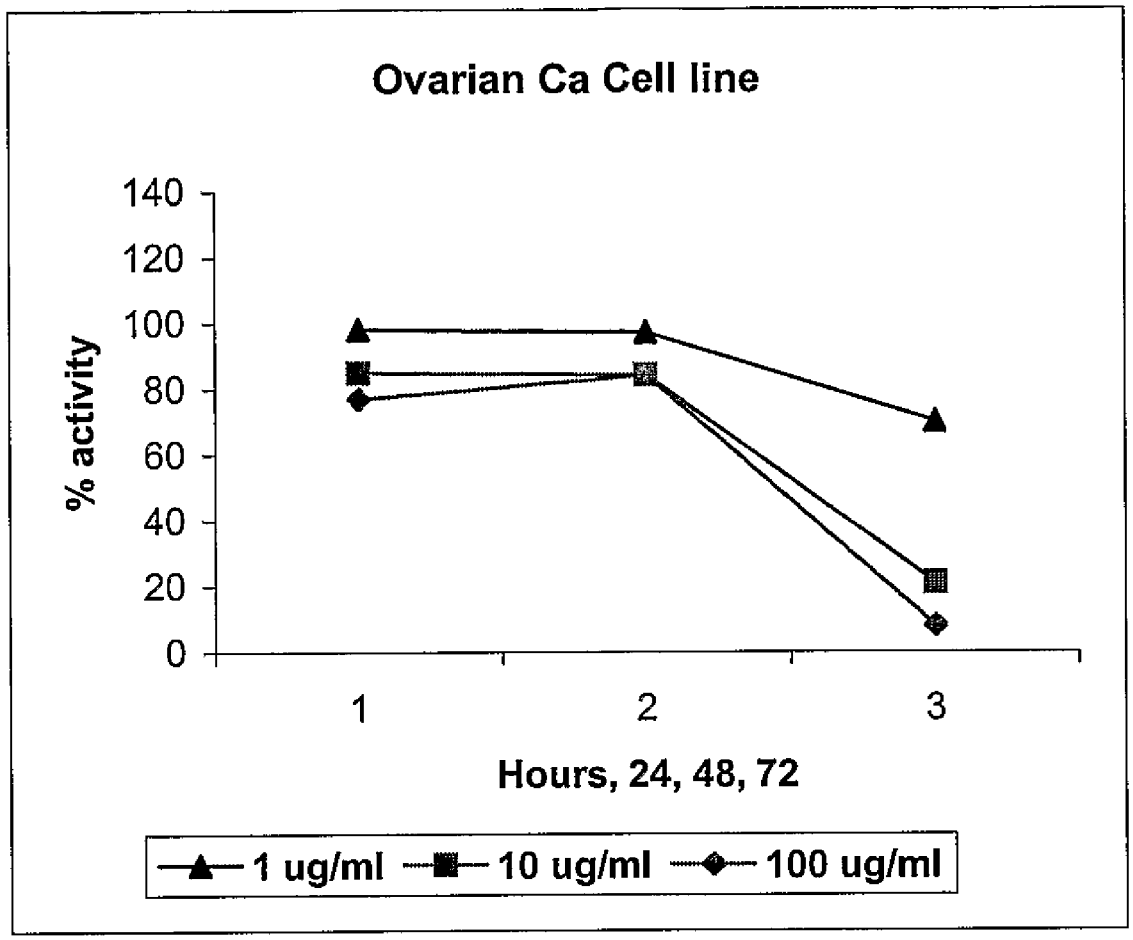
FIGS. 3A-3C are graphical representations of percentage of activity of ovarian cancer cells, human skin fibroblasts and human lymphocytes treated with a crude chloroform extract of *Calomeria amaranthoides* at varying concentrations.

Cell viability was also assessed following addition of Alamar Blue (BioSource, Europe) (Page et al., 1993) in the 24-well plates (100 µl Alamar Blue and 1 ml medium/well). The supernatant was transferred to 96-well plates and absorbance measured by a cytofluor machine. FIG. 3A shows percentage of activity of ovarian cancer cells (van Haaften-Day et al., (1990) Cancer 65(8), 1753-61) treated with crude chloroform extract at varying amounts. Similar results were seen when a dichloromethane extract was used on the cancer cells.

Figure 3B:
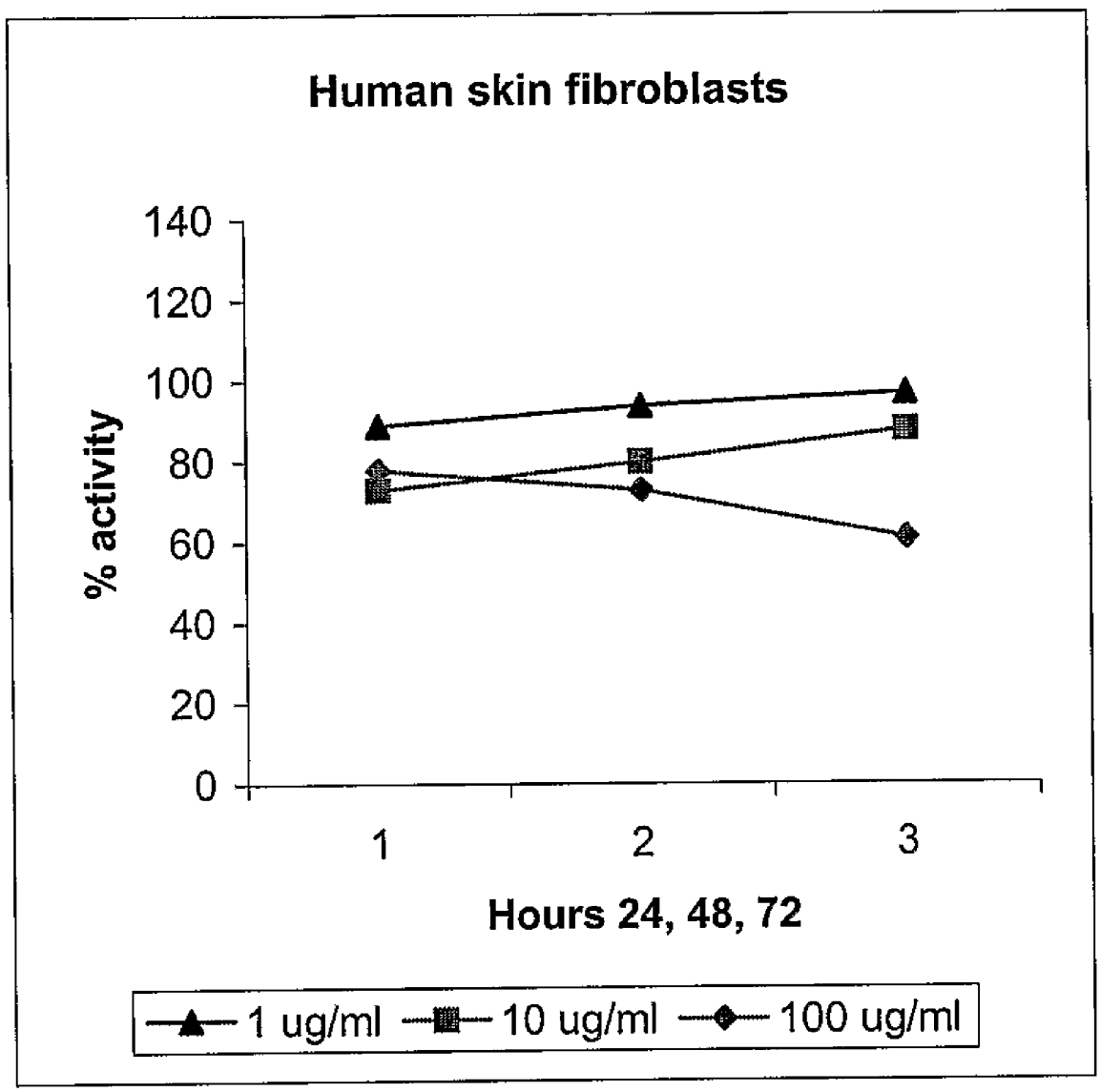
Figure 3C:
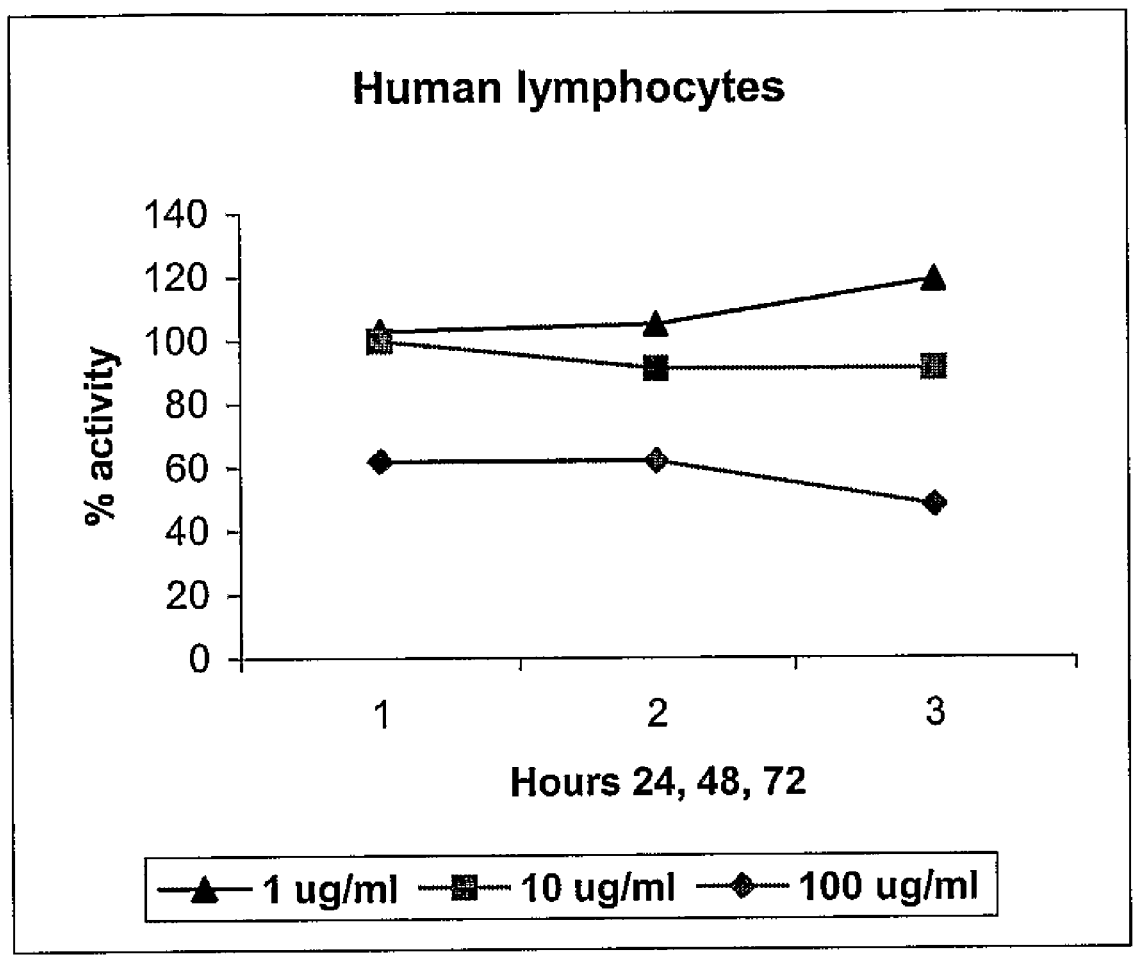

FIG. 3B shows percentage of activity of normal skin fibroblasts grown in 24-well plates, treated for 72 hours with different concentrations of crude extract and FIG. 3C shows percentage of activity of human lymphocytes, grown in 96-well plates (Ansar Ahmed., 1994) over 72 hours with the different concentrations of the extract.

Figure 4A:
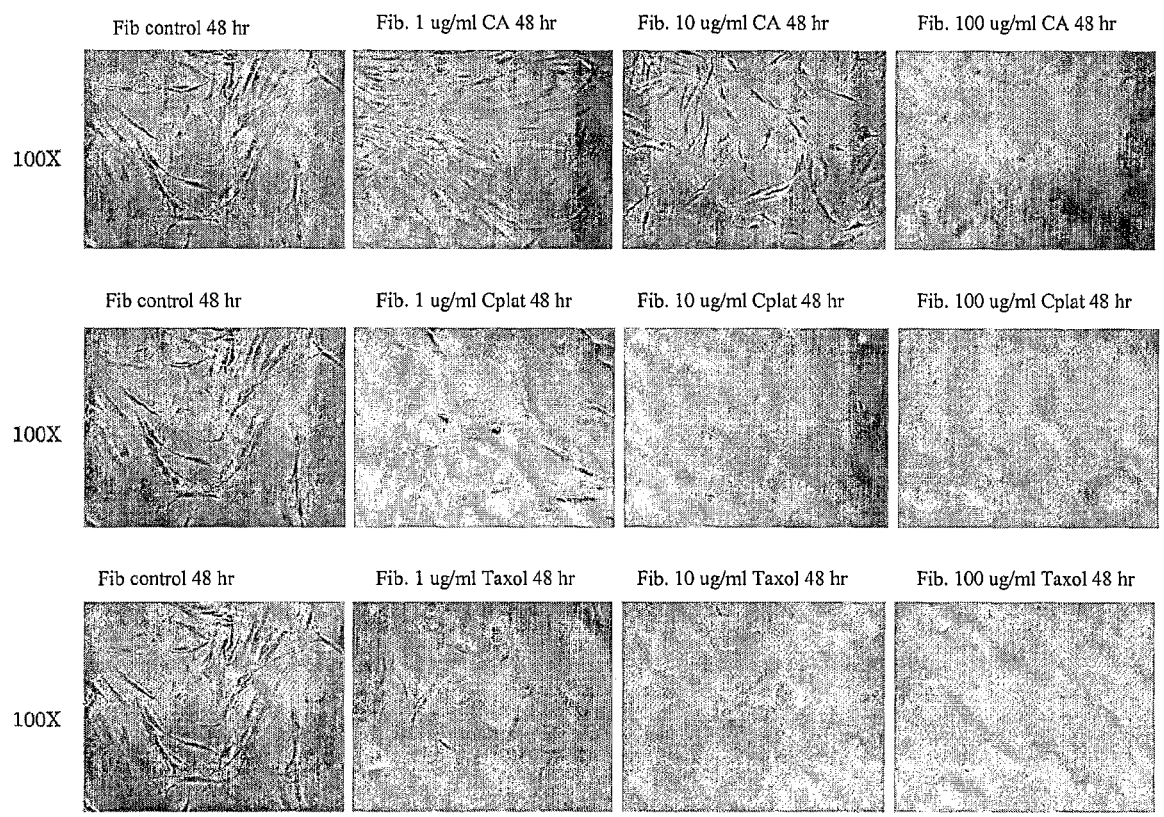
FIG. 4A show photomicrographs of human skin fibroblasts (Fib.) treated with 1, 10 or 100 μg/ml of *Calomeria amaranthoides* extract, Cisplatinum, or Docetaxol. Photomicrographs were taken at 48 hours.
Figure 4B:
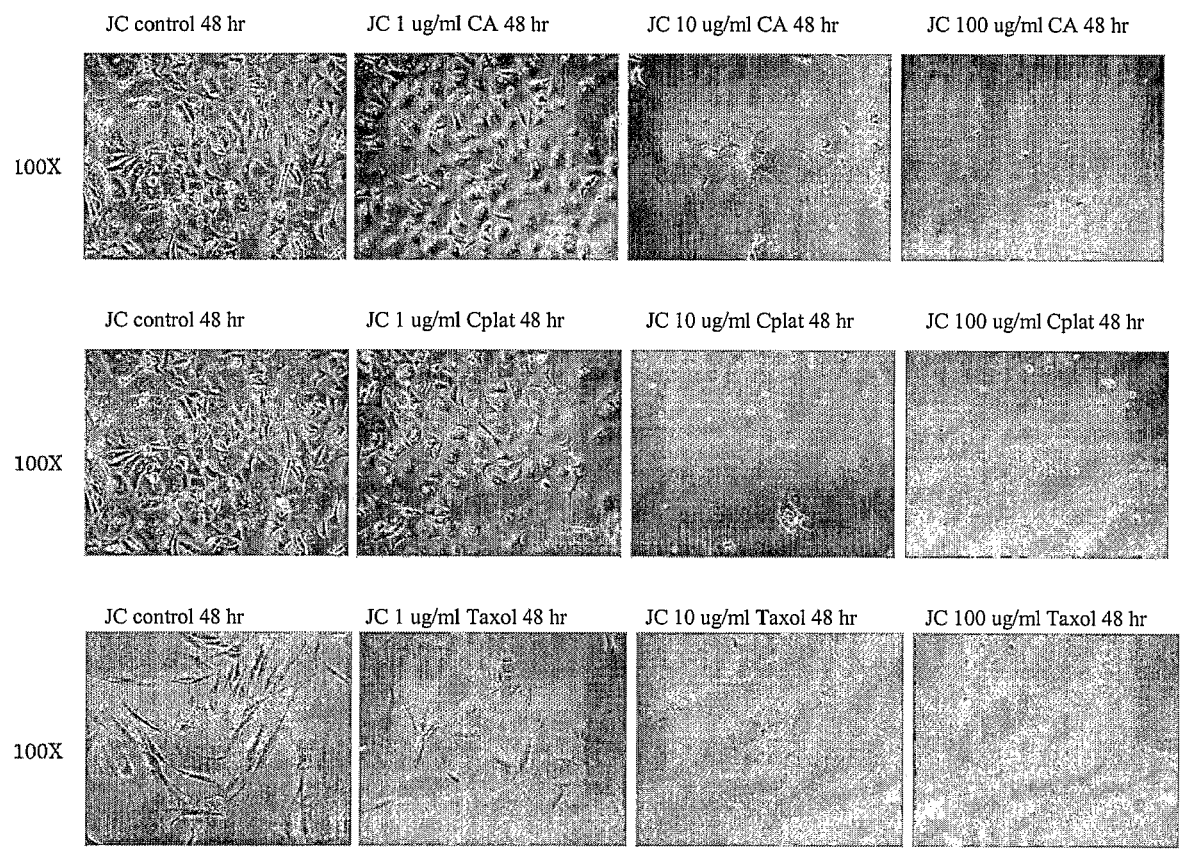
FIG. 4B show photomicrographs of JC ovarian cancer cells treated with 1, 10 or 100 μg/ml *Calomeria amaranthoides* extract, Cisplatinum or Docetaxol. Photomicrographs were taken at 48 hours post treatment.

Cytotoxity of the *Calomeria amaranthoides* extract was also compared with that of Cisplatinum (Pharma chemie, Haarlem) and Docetaxol (Aventis Pharma, Hoevelaken) using human skin fibroblasts and the ovarian cancer line JC (Van Haaften-Day et al, 1983 Cancer Res. 43(8), 3725-31) (FIG. 4). Fibroblasts were treated with 1, 10 or 100 µg of the *Calomeria* extract ("CA"), Cisplatinum ("Cplat") or Docetaxol ("Taxol") and cell viability observed at 48 hours following addition of treatment, and recorded by photomicrography (FIG. 4A). Similarly, the ovarian cancer cell line JC was treated with 1, 10 or 100 µg *Calomeria* extract, Cisplatinum or Docetaxol and cell viability was observed and recorded at 48 hours (FIG. 4B).

Whereas cytotoxicity in fibroblasts by Cisplatinum or Docetaxol may be observed at a dose of 1 µg at 48 hours, with a greater reduction in cell viability occurring with 10 µg and 100 µg of either compound, the *Calomeria* extract is seen to exhibit less cytotoxicity in fibroblasts, with 1 µg extract showing only minimal cytotoxicity, and even at 10 µg (FIG. 4A). The *Calomeria* extract is therefore less cytotoxic in cells representative of a normal phenotype than Cisplatinum or Docetaxol.

In contrast, the *Calomeria* extract at 1, 10 or 100 µg shows similar toxicity to Cisplatinum at 1, 10 or 100 µg in the JC ovarian cancer cell line (FIG. 4B). JC cells appeared more resistant to Docetaxol. Docetaxol appears to be less cytotoxic than either the *Calomeria* extract or Cisplatinum when the treatments are compared at the 10 µg dosage level for 48 hours.

Accordingly, the *Calomeria* extract exhibits greater selectivity for the ovarian cancer cell line than either of Cisplatinum or Docetaxol, showing significantly less effect on cells representative of the normal phenotype at dosages that were cytotoxic in cancer cells.

The extracts of *Calomeria* were found to be causing apoptotic cell death, characterised by morphological changes such as cell and nucleus shrinkage, condensing and fragmentation.

The cytotoxicity of the extracts in the $L_{1210}$ cancer cell line is shown in Table 1.

TABLE 1

| Treatment | Dose (µg/mL) | Growth inhibitory Index (%) IC50 (µg/mL) 48 hr after drug treatment in $L_{1210}$ cell line |
|---|---|---|
| Control | | |
| Crude chloroform extract | 1 | 9 |
| | 10 | 93 |
| | 100 | 100 |
| 95% ethanol extract | 1 | 6 |
| | 10 | 76 |
| | 100 | 100 |
| | III-P133 | |

It was also noted that leaves taken from plants that were 2 years old produced extracts that were more cytotoxic than extracts prepared from leaves taken from the same plants at 1 year old.

Example 5

HPLC Separation of Crude Extract of *Calomeria amaranthoides*

Crude extract, as well as fractionated extract, of the leaves of two-year old plants of *Calomeria amaranthoides* were analysed using an HPLC protocol.

Chloroform/methanol/water 1:1:1 (v/v/v) were used to achieve a clear two-phase separation of crude leaf extract. The chloroform layer was then dried with anhydrous sodium sulphate, filtered and then blown dry. The resultant residue was then dissolved in HPLC injection solvent (hexane:dioxane 99.5:0.5, v/v).

This approach yielded a clear solution in the above solvent. Separation was performed on Silica 5Si60 straight-phase HPLC-columns using hexane:dioxane 99.5:0.5, v/v as eluent (run time 30 min, flow rate 2.5 ml/min, UV at range of wavelengths nm). 50-100 µg of crude sample was injected for each run on analytical 250*4.6 id min columns.

In addition to analysing crude extract, concentrated fractions derived from column chromatography were also analysed by straight phase HPLC.

The readouts resulting from HPLC analysis of Fraction 2, run at different wavelengths, are shown in FIGS. 2A-2J.

Alternatively, crude extract was chromatographed on an LC-18-DB column (reverse-phase), 5 µl (250*4.6 id mm). Separation was performed with a sodium phosphate buffer 50 mM and 10 mM heptane sulfonic acid (pH was 3.4; run of 30-50 min.; flow rate 1 ml/min., UV wavelength 254 nm). 20 µl extract was injected.

Figure 2A:
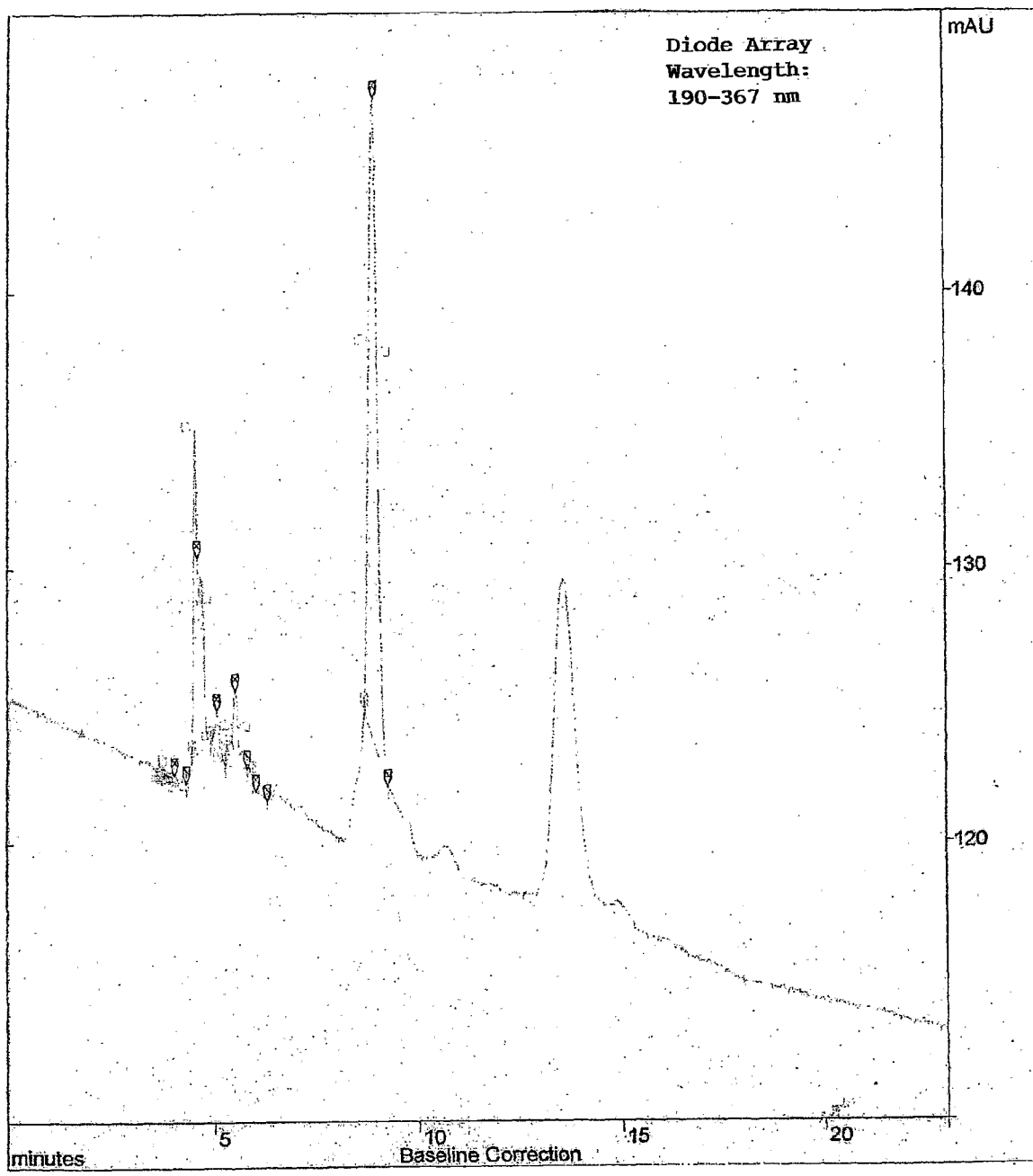
FIGS. 2A-2J show an HPLC trace of fraction 2 (collected from column chromatography of *Calomeria amaranthoides* extract), analysed on Silica 5Si60 straight-phase HPLC-columns and detected at different wavelengths.
Figure 2B:
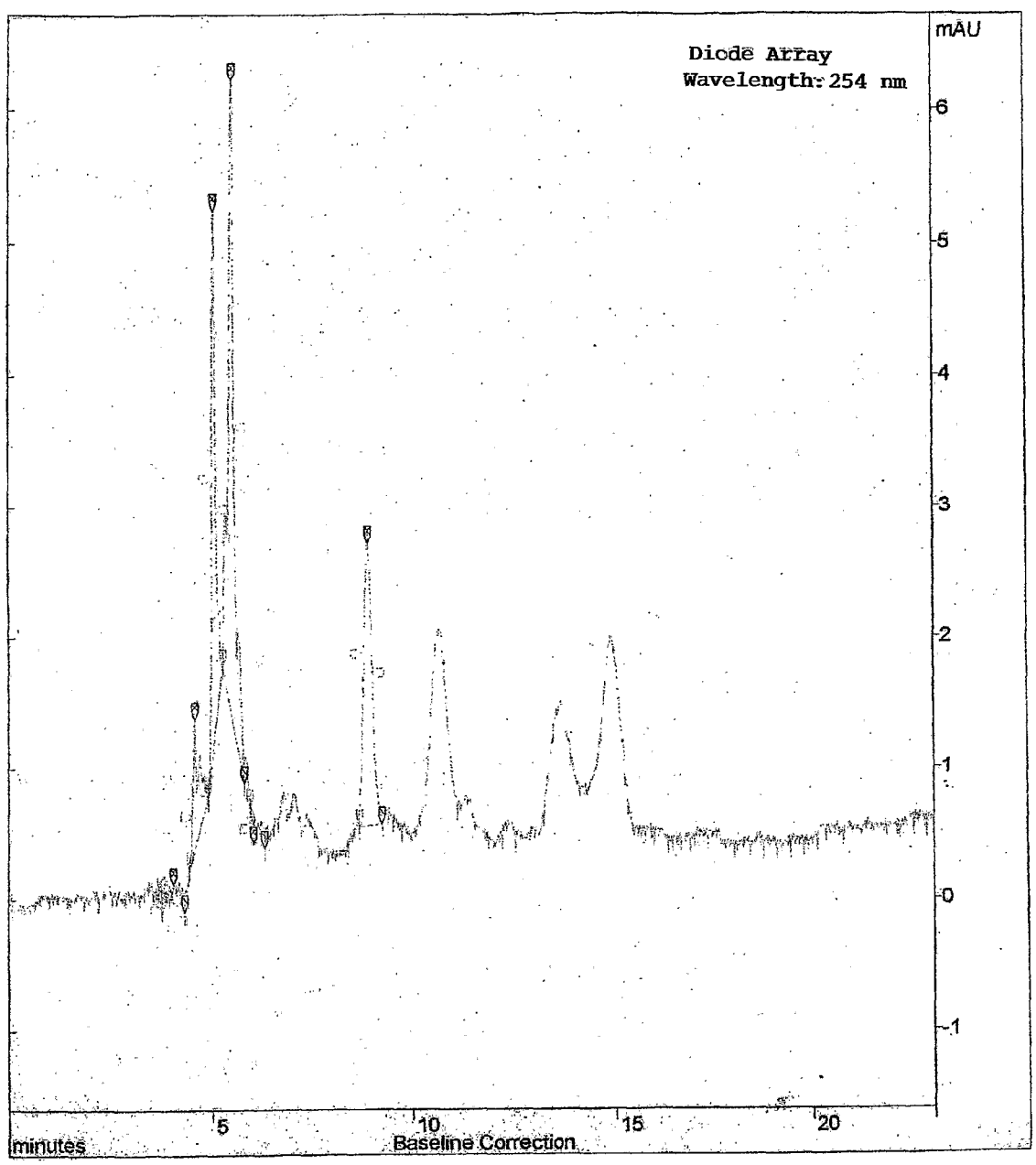
Figure 2C:
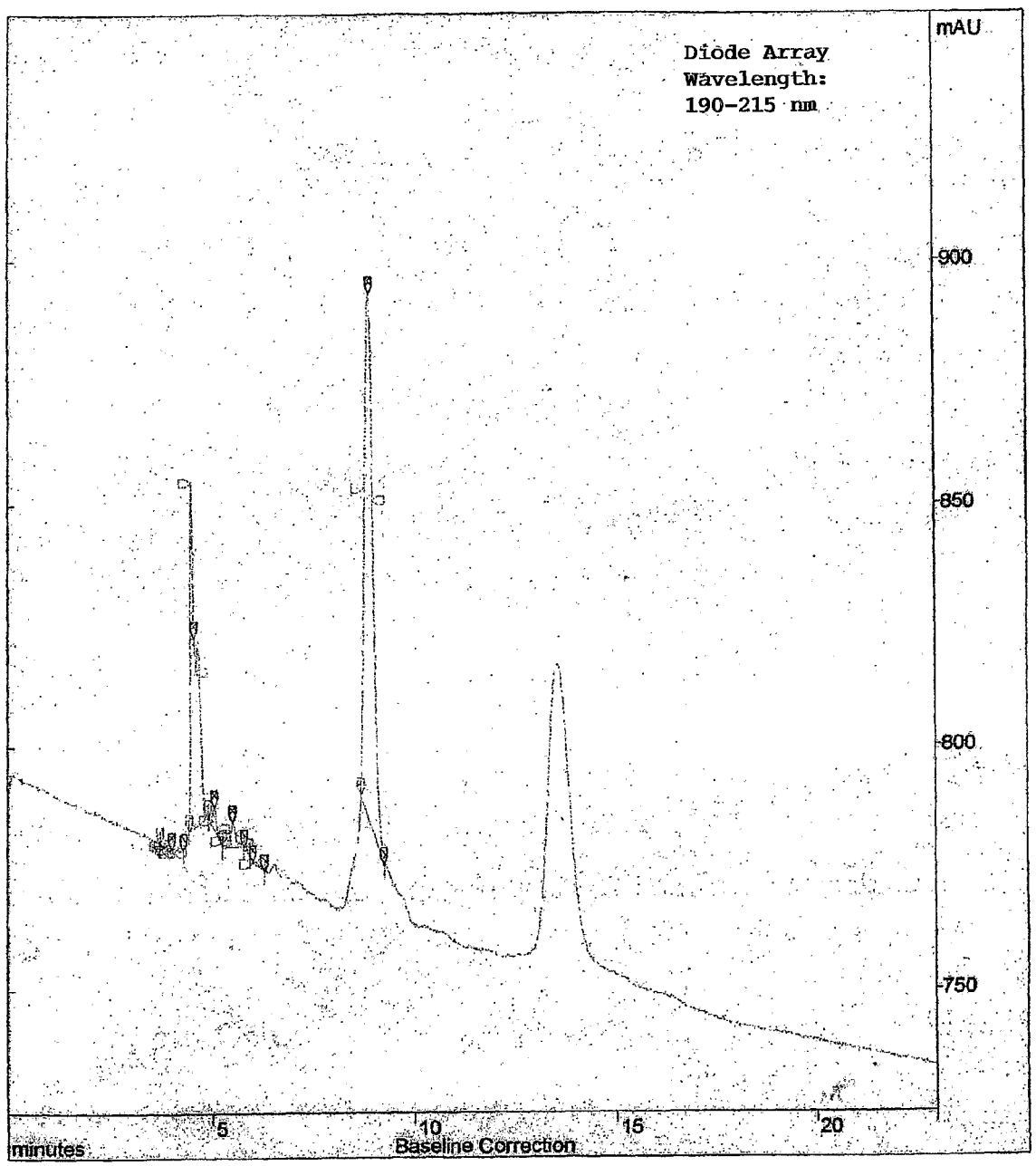
Figure 2D:
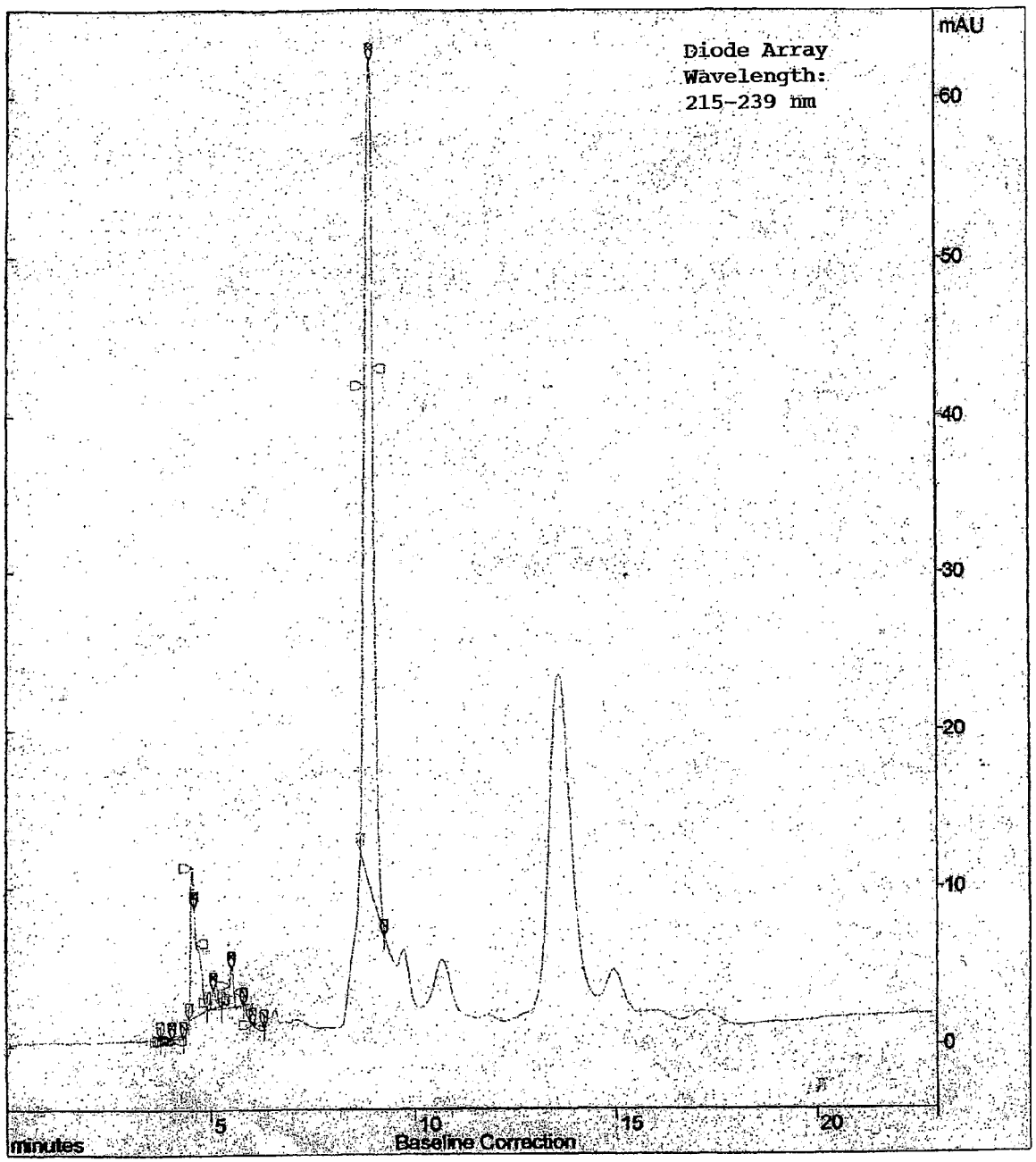
Figure 2E:
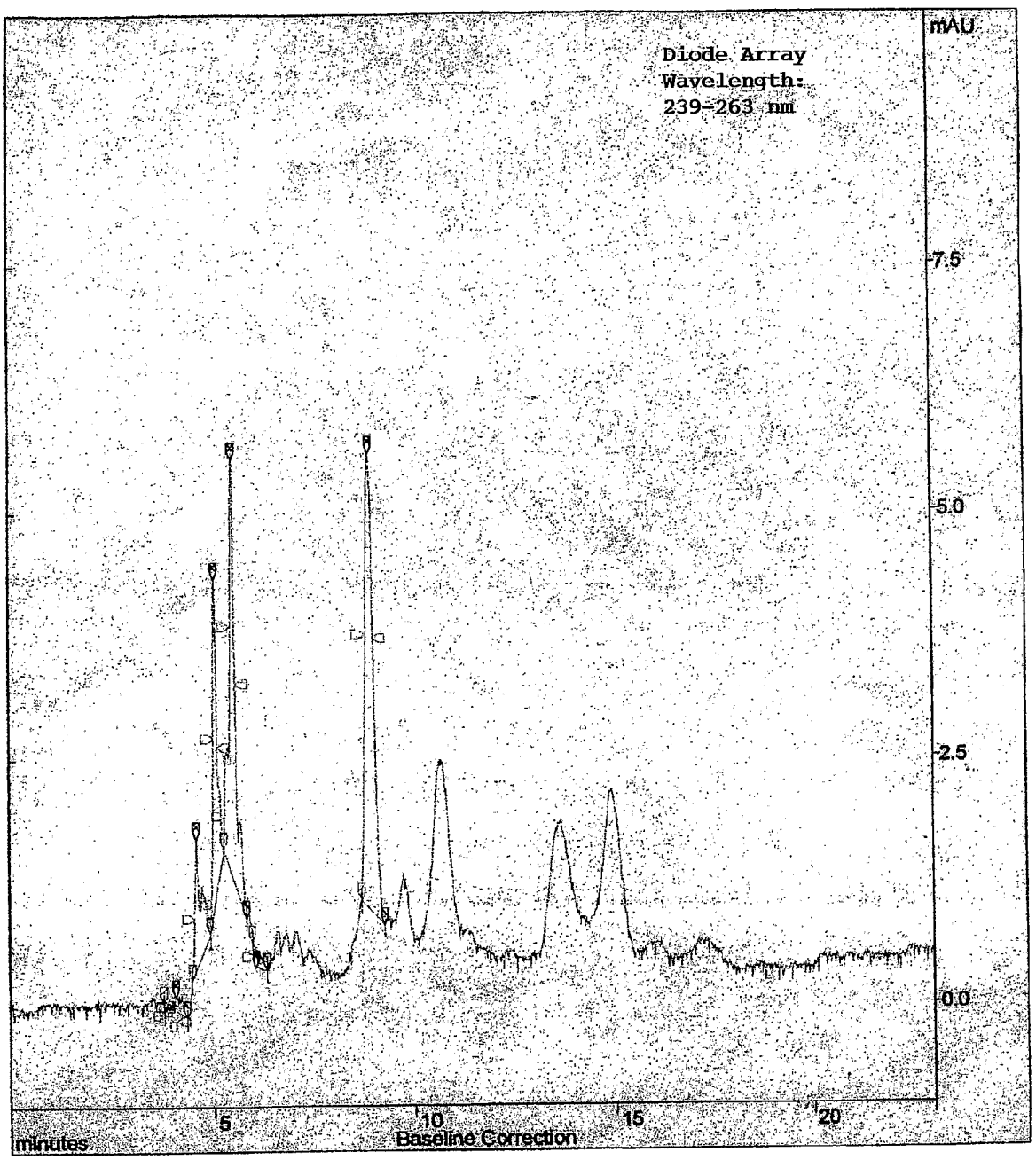
Figure 2F:
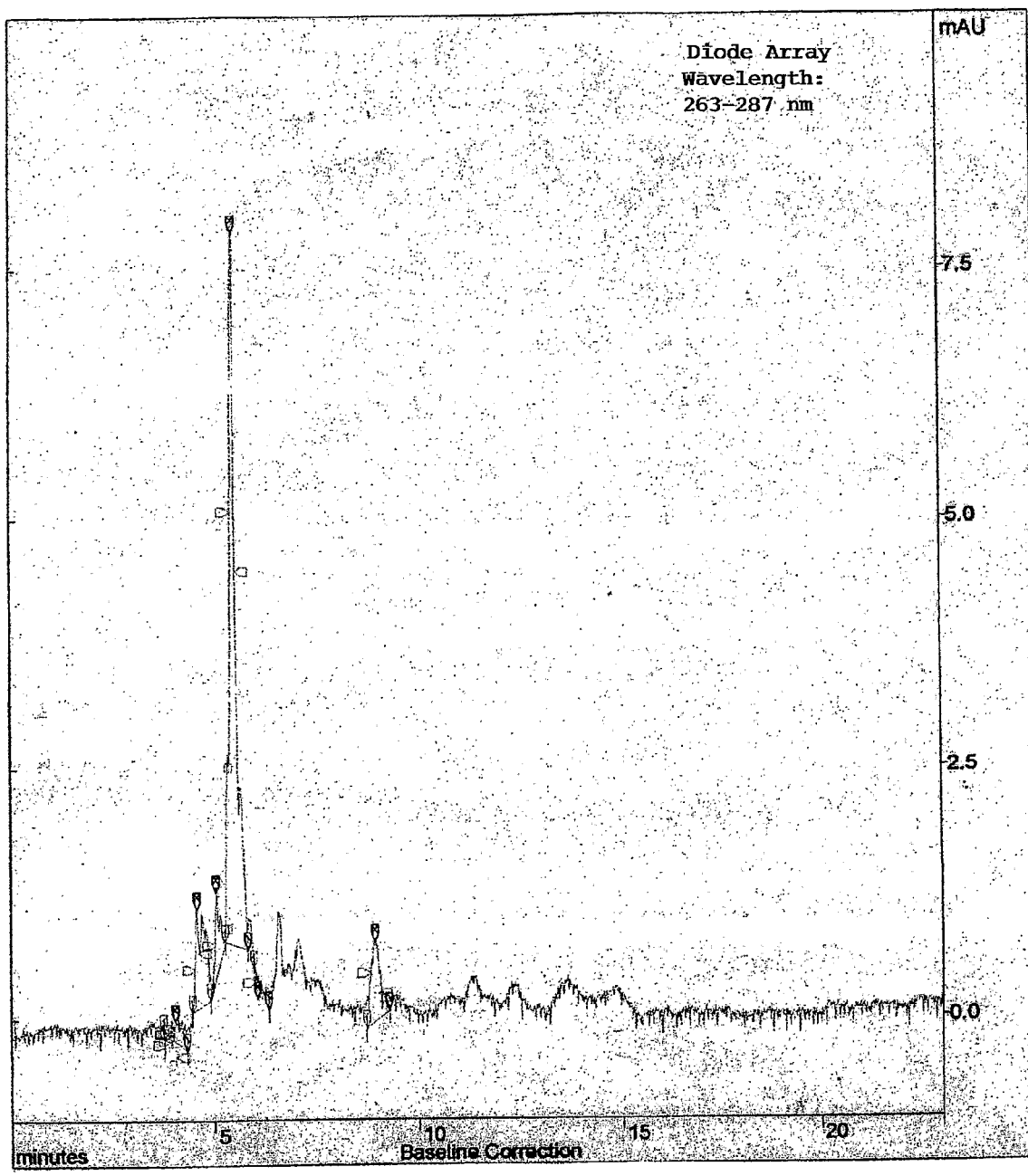
Figure 2G:
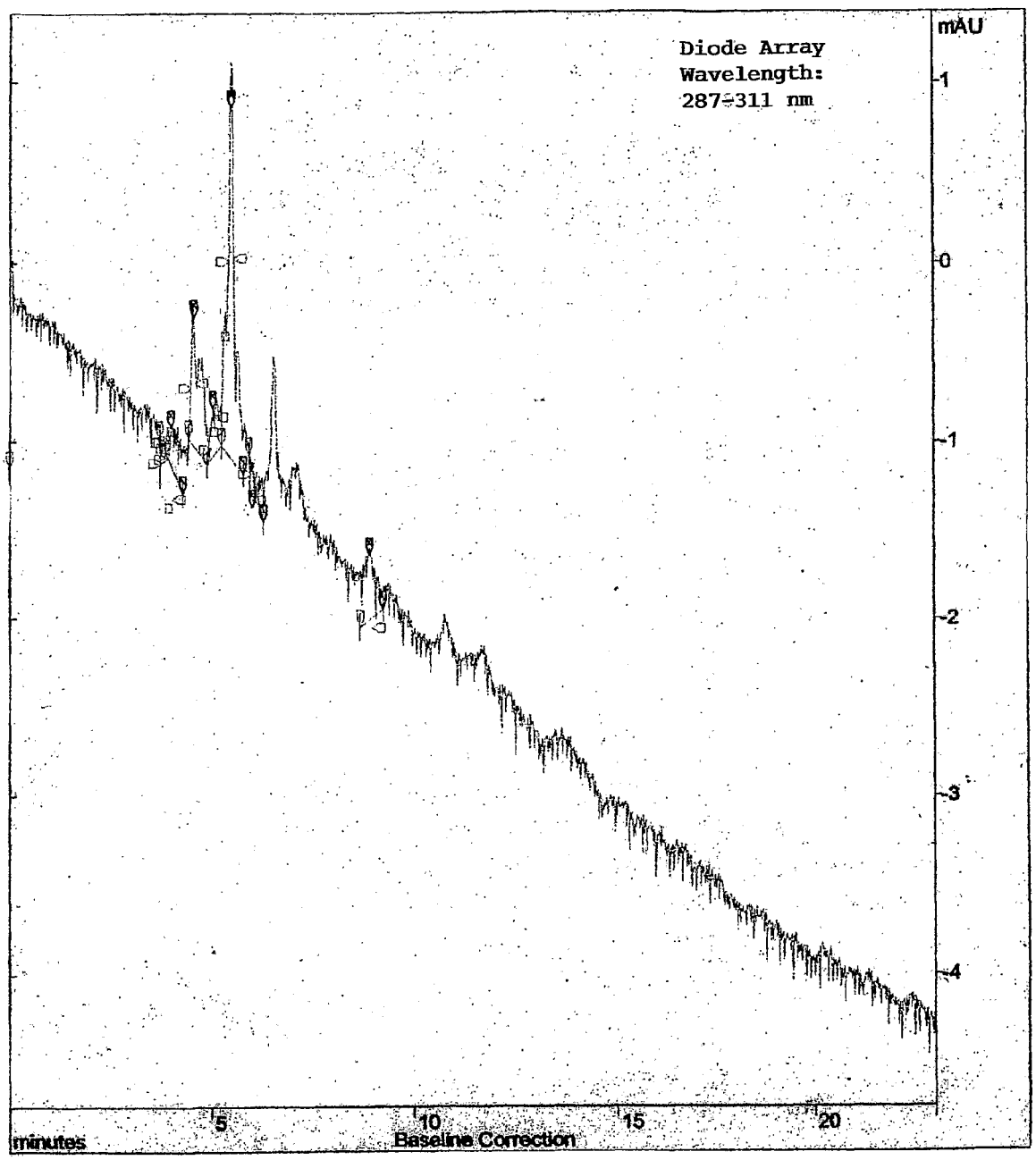
Figure 2H:
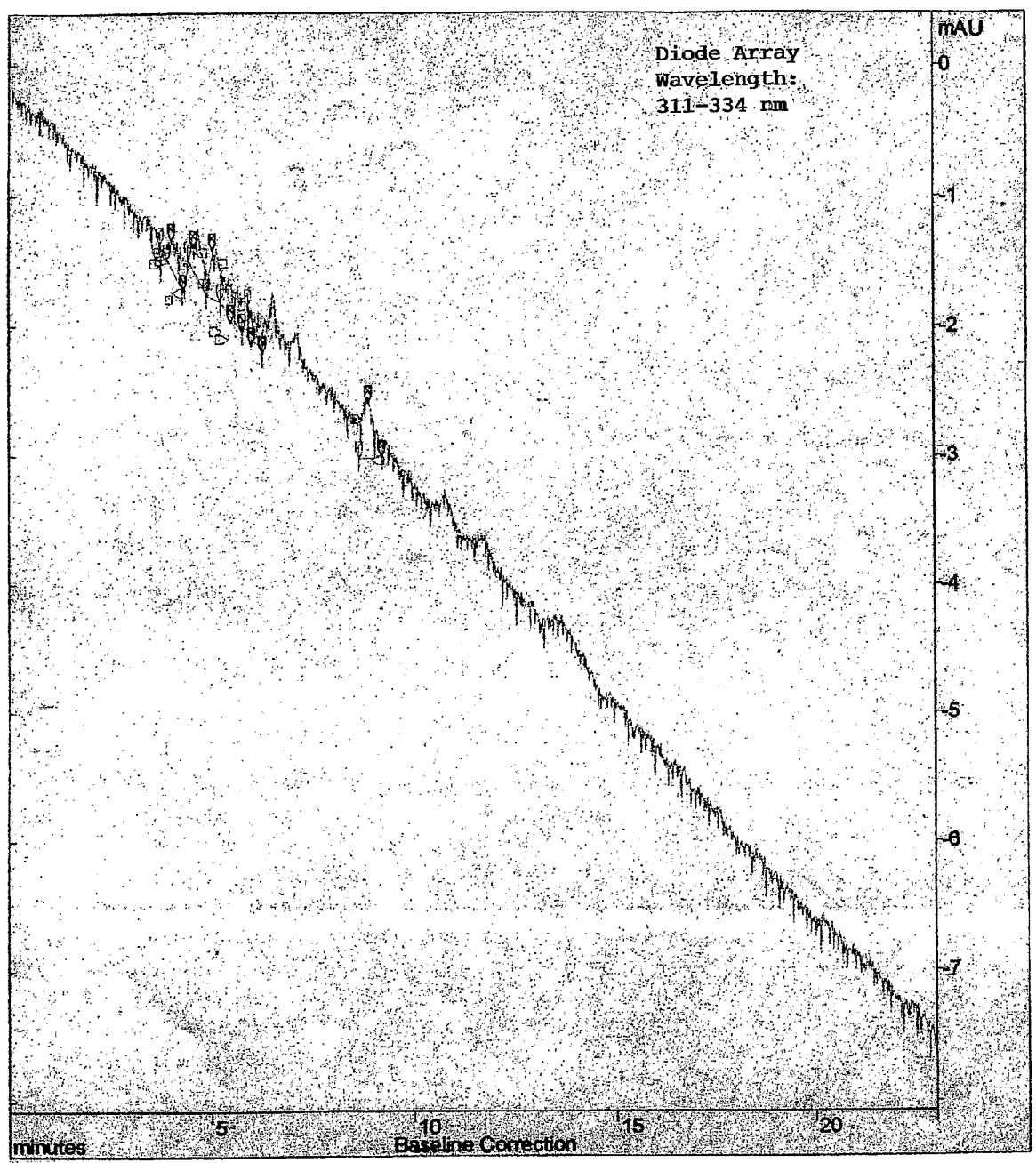
Figure 2I:
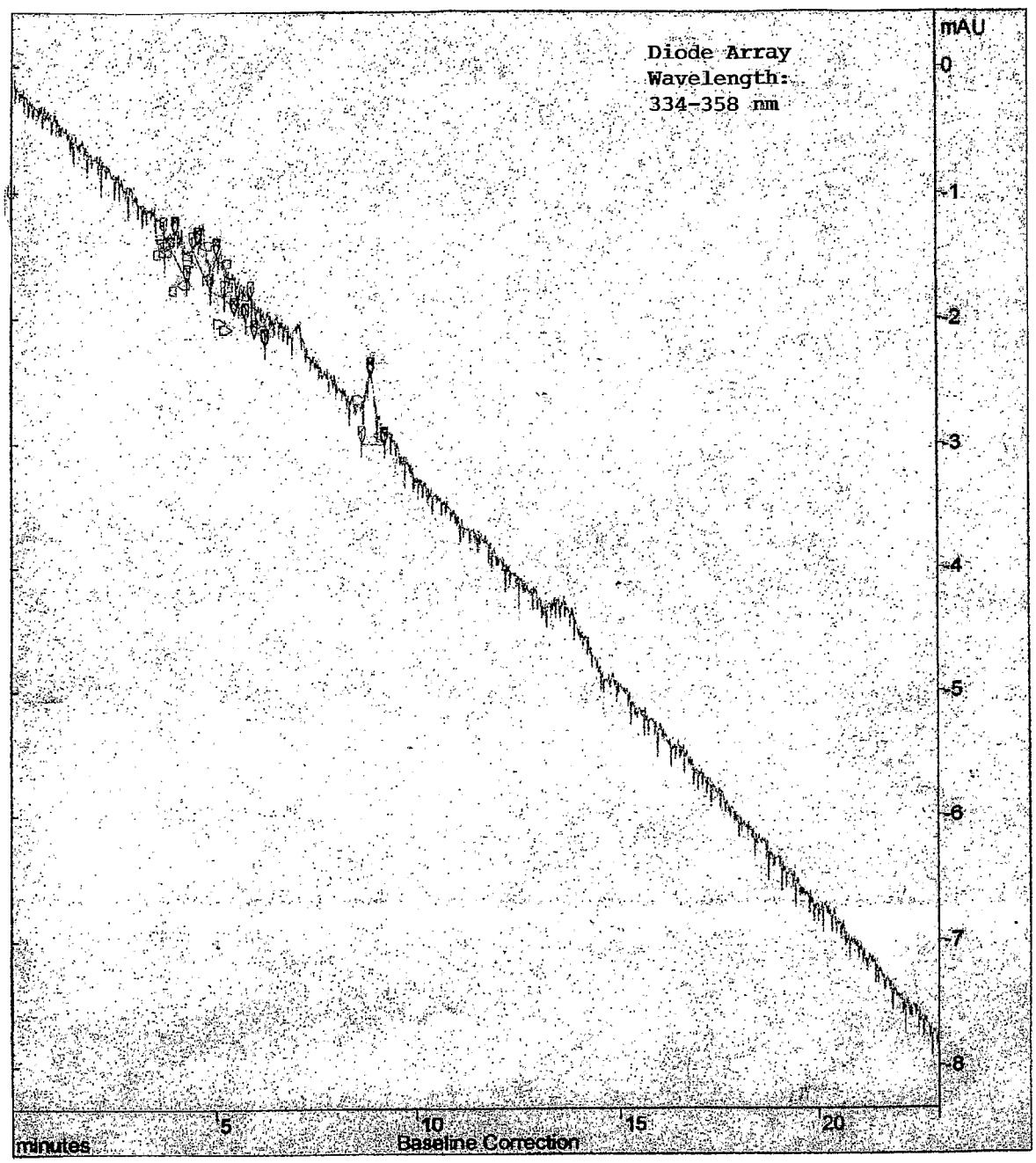
Figure 2J:
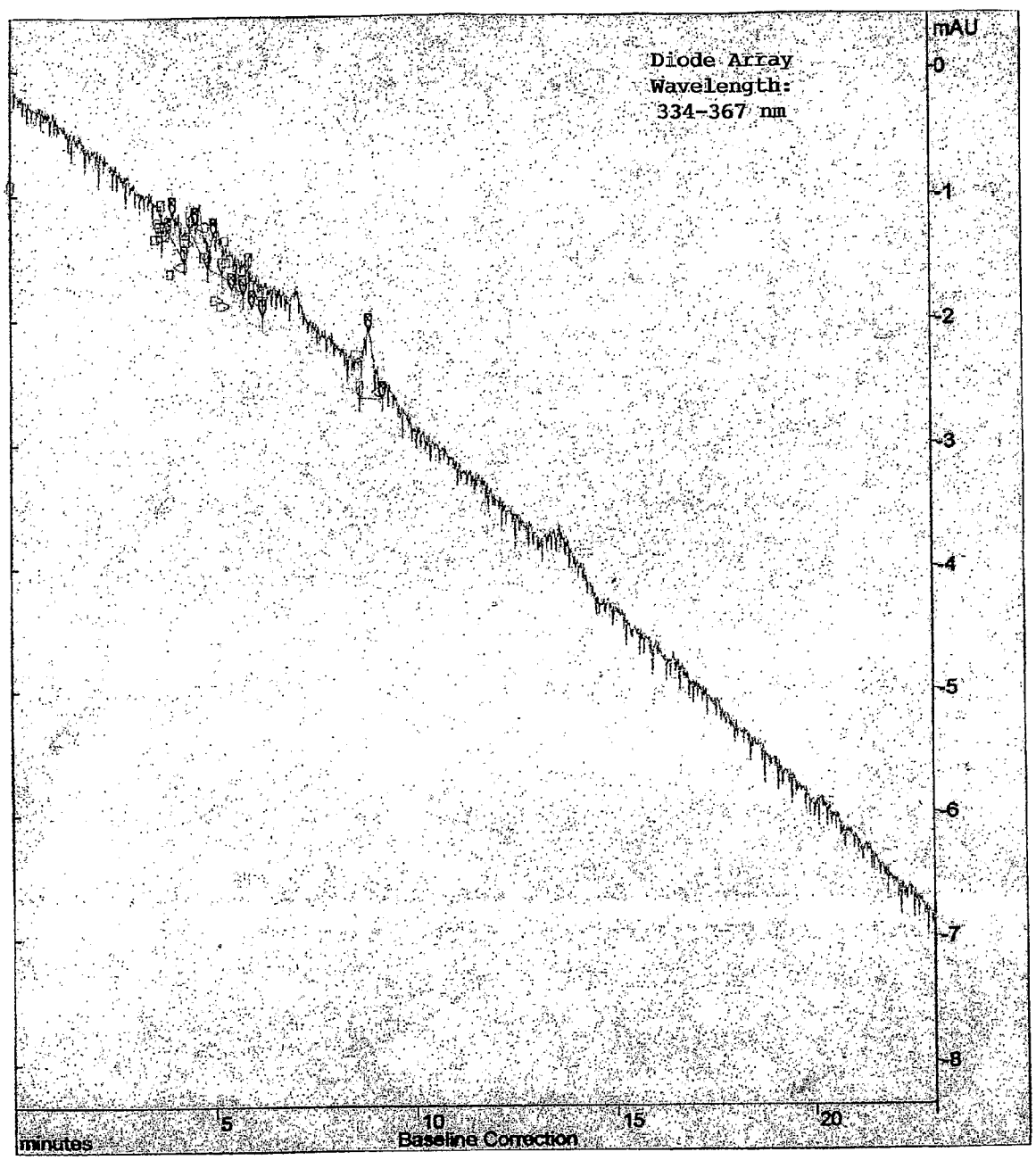
Figure 2K:
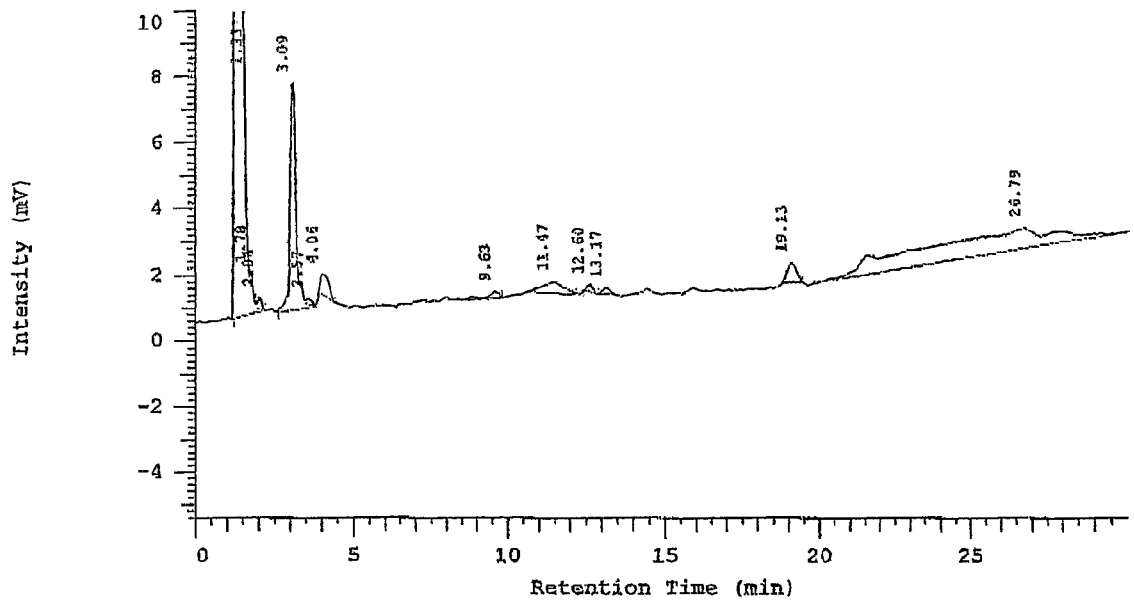
FIGS. 2K-2M shows HPLC traces of a crude chloroform extract of *Calomeria amaranthoides* analysed on an LC-18-DB column (reverse-phase).
Figure 2L:
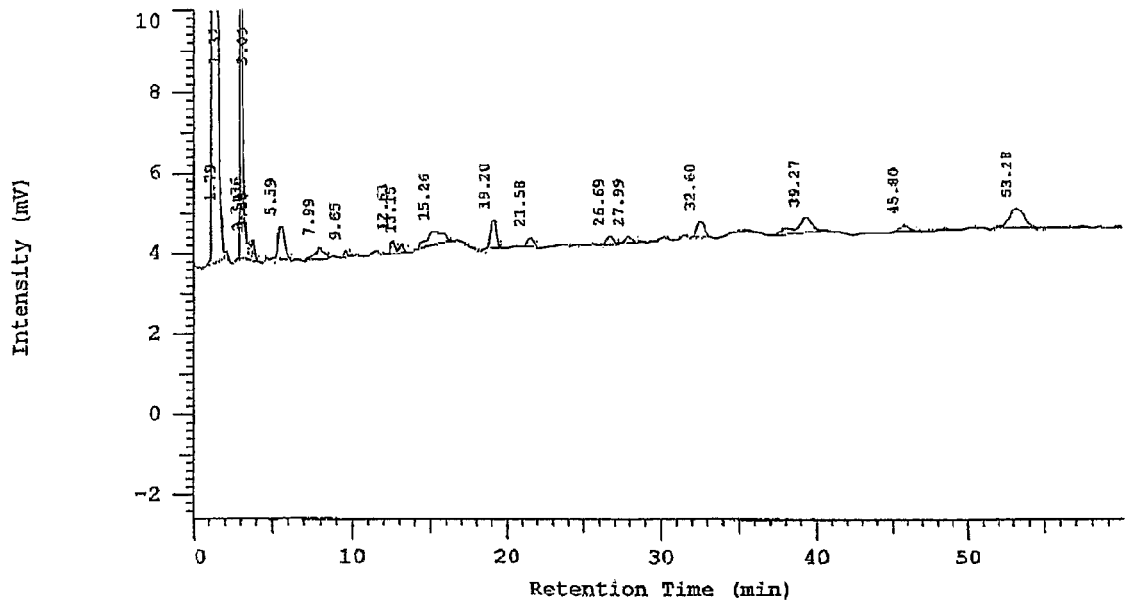
Figure 2M:
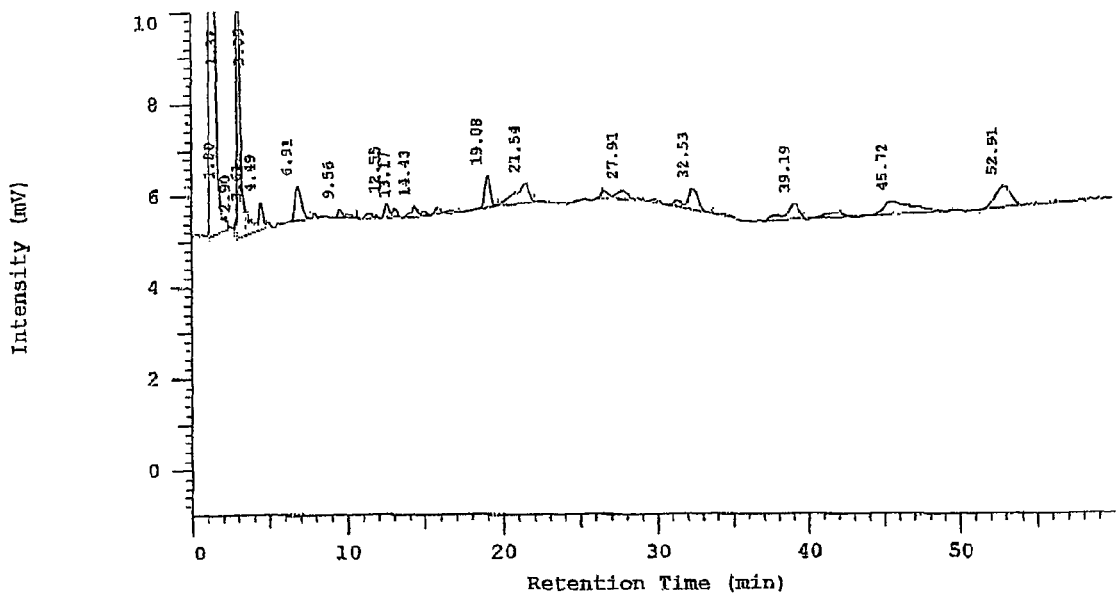

The resulting HPLC readout is shown in FIG. 2K. Repeat runs are shown in FIGS. 2L and 2M with different run times.

Example 6

Nuclear Magnetic Resonance Imaging of Chloroform Fractions of *Calomeria amaranthoides*

The crude chloroform extract derived from *Calomeria amaranthoides* and fractions purified by column chromatography under gravity were analysed using nuclear magnetic resonance spectroscopy on a Varian Gemini 300 NMR spectrometer. $^1$H NMR was performed at 300 MHz and $^{13}$C NMR at 75 MHz.

Figure 5A:
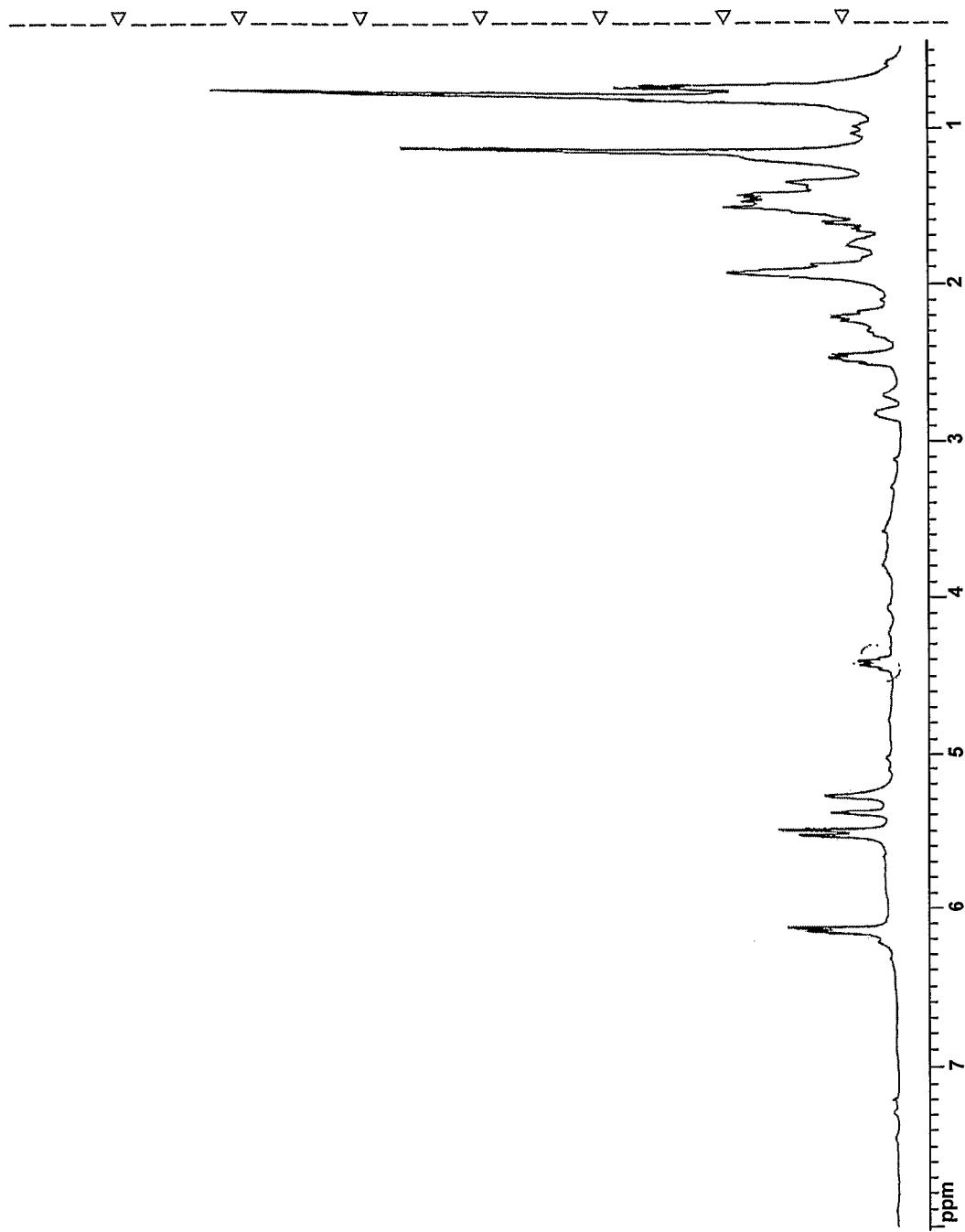
FIG. 5A shows a $^1$H NMR spectrum from fraction 12 (collected from column chromatography of *Calomeria amaranthoides* extract).
Figure 5B:
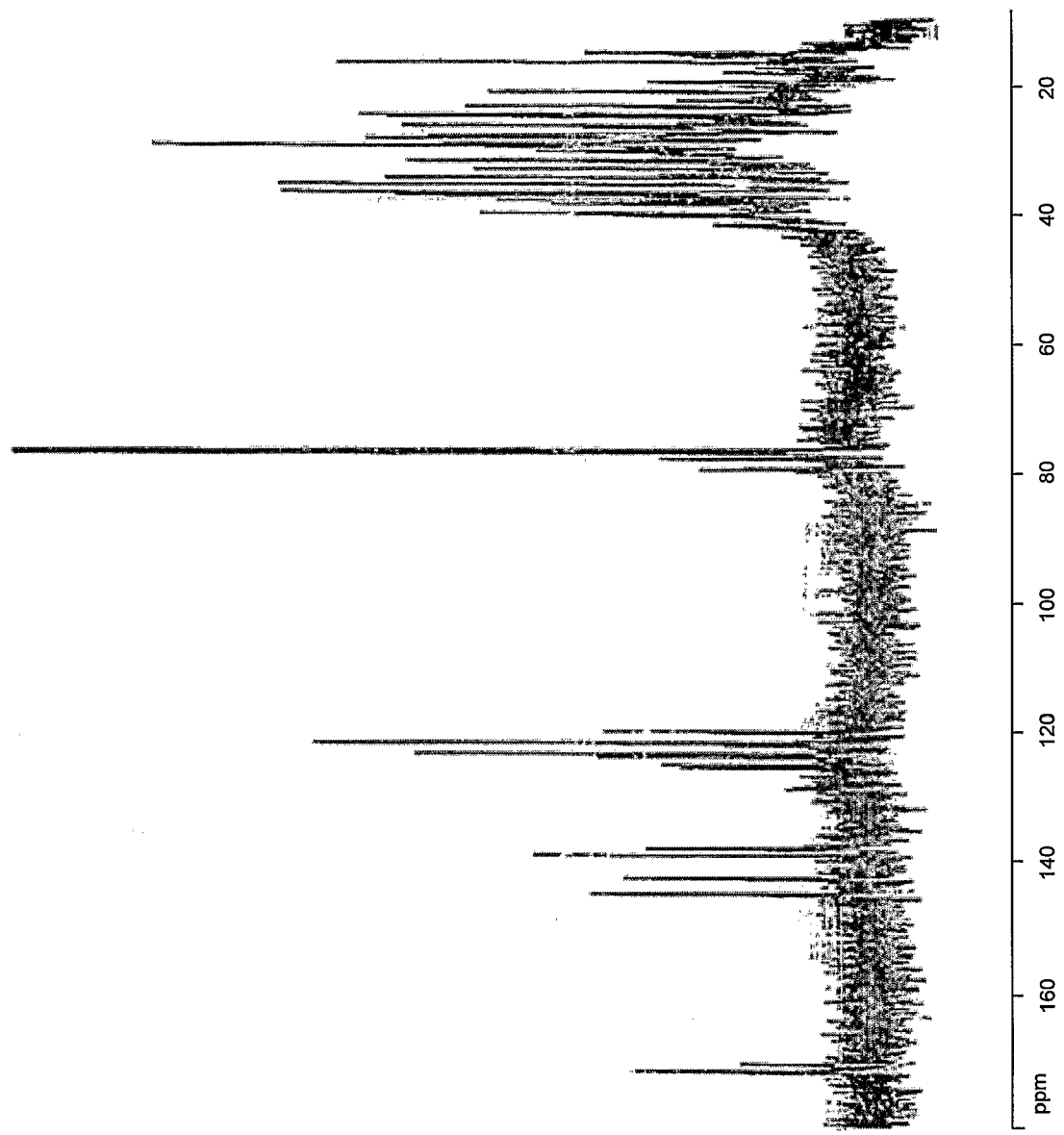
FIG. 5B shows a $^{13}$C NMR spectrum from fraction 12 (collected from column chromatography of *Calomeria amaranthoides* extract).

An analytical amount of the 13 and 57 fractions from crude plant extract were suspended in 0.4 ml of PBS/D$_2$O in a 5 mm diameter NMR tube on top of a plug of glass wool, then placed into a 5 mm-diameter NMR tube containing 1 mmol/L of p-aminobenzoic acid in PBS/D$_2$O which served as a reference. $^1$H NMR spectra were recorded at 37° C., using a standard 5 mm diameter proton head. The $^1$H NMR spectrum for fraction 12 is shown in FIG. 5A, and the $^{13}$C NMR spectrum for fraction 12 is shown in FIG. 5B.

The $^1$H NMR spectrum derived from fraction 12 was characteristic of the following eudesmanolide-like structures:

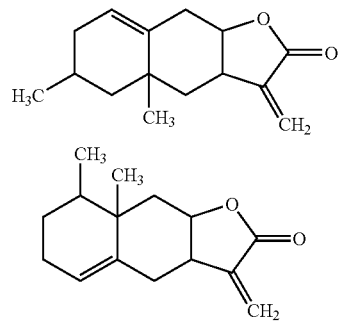

Example 7

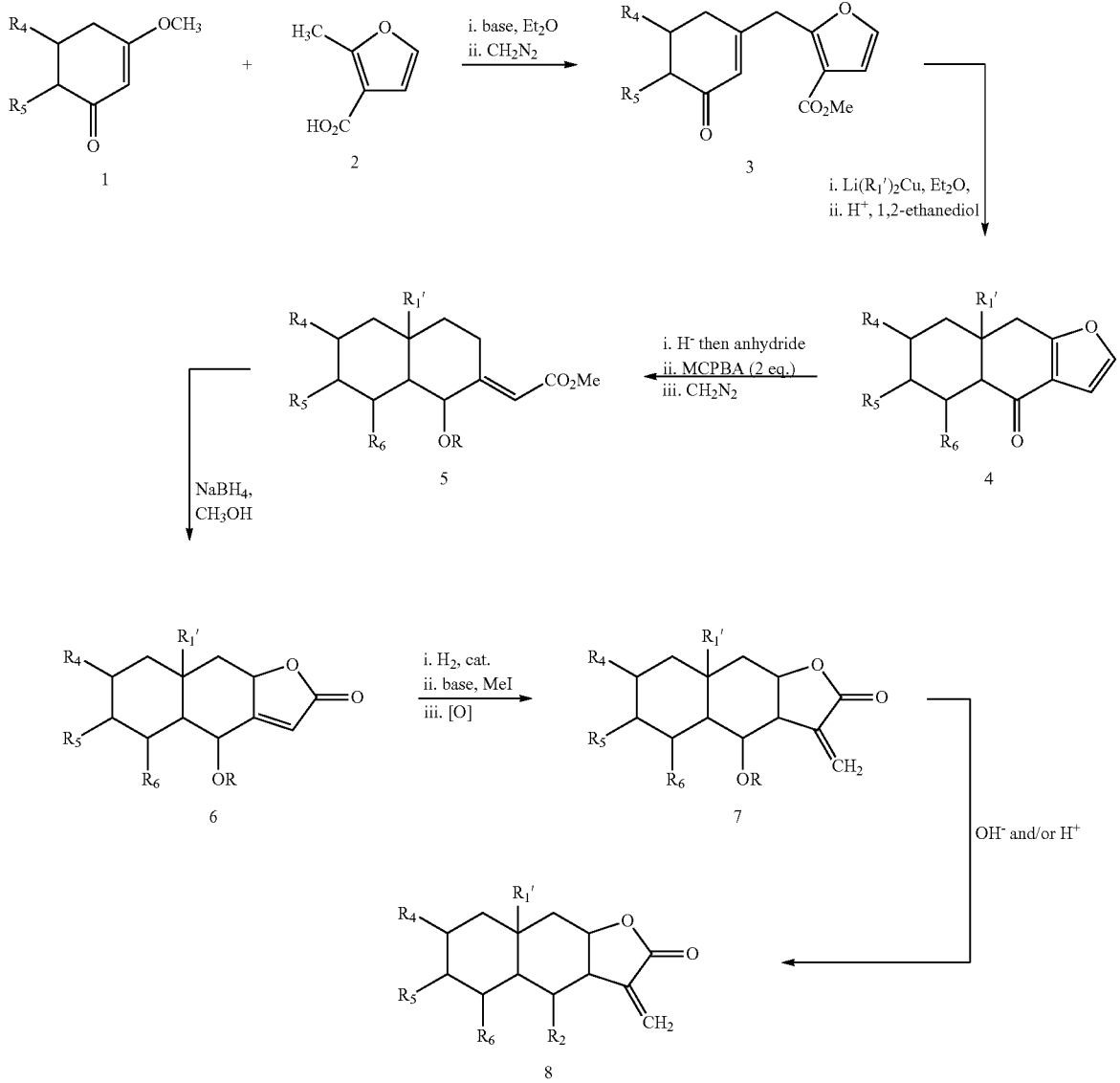

Synthetic Scheme for Compounds of Formula I

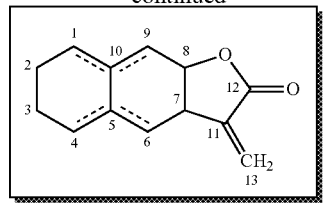

Numbering scheme

Treatment of 2-methyl-3-furoic acid (2) with a suitable base is followed by trapping of the dianion so generated with methoxycyclohexenone 1. The product obtained from this reaction is treated with an excess of diazomethane to afford synthon 3. Ester 3 is converted directly into tricyclic compound 4 by treatment with $Li(R_1')_2Cu$ followed by selective protection of the $C_4$ ketone. Reduction of the $C_6$ carbonyl is then followed by protection of the ensuing hydroxyl. This material is then treated with two equivalents of m-chloroperbenzoic acid (MCPBA) followed by an excess of diazomethane to afford the ring-opened methyl ester 5. Treatment of 5 with $NaBH_4$ in methanol affords tricyclic enone 6. Subjection of this enone to catalytic hydrogenation followed by methylation at $C_{11}$ and oxidation of the methyl group affords 7. Global deprotection of the protecting groups then affords compound 8.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. An extract of *Calomeria amaranthoides* which exhibits cytotoxic activity in vitro towards cells exhibiting conditions associated with hyperproliferative cellular division, wherein the extract is selected from a chloroform, petrol ether, dichloromethane, ethylacetate, and ethanol extract.

2. An extract of *Calomeria amaranthoides* which exhibits cytotoxic activity in vitro towards cells exhibiting conditions associated with hyperproliferative cellular division, wherein the extract is a chloroform extract.

3. An extract of *Calomeria amaranthoides* which exhibits cytotoxic activity in vitro towards cells exhibiting conditions associated with hyperproliferative cellular division, wherein the extract is an organic solvent-derived extract, and wherein the extract exhibits a proton NMR spectrum as shown in FIG. 5A, and a $^{13}C$ NMR spectrum as shown in FIG. 5B.

4. A pharmaceutical composition comprising a pharmaceutically effective amount of an extract of *Calomeria amaranthoides* which exhibits cytotoxic activity in vitro towards cells exhibiting conditions associated with hyperproliferative cellular division, and a pharmaceutically acceptable carrier.

5. A method of inhibiting growth or eliminating cells exhibiting conditions associated with hyperproliferative cellular division comprising administering to the cells in vitro an effective amount of an extract of *Calomeria amaranthoides* which exhibits cytotoxic activity in vitro towards cells exhibiting conditions associated with hyperproliferative cellular division.

6. An organic solvent-derived extract of *Calomeria amaranthoides* comprising at least one sesquiterpene lactone, wherein the extract exhibits cytotoxic activity in vitro towards cells exhibiting conditions associated with hyperproliferative cellular division.

* * * * *